US008580944B2

(12) United States Patent
Klinman et al.

(10) Patent No.: US 8,580,944 B2
(45) Date of Patent: Nov. 12, 2013

(54) SUPPRESSORS OF CPG OLIGONUCLEOTIDES AND METHODS OF USE

(75) Inventors: Dennis M. Klinman, Potomac, MD (US); Rainald Zeuner, Kiel (DE); Mayda Gursel, Rockville, MD (US); Ihsan Gursel, Rockville, MD (US); Daniela Verthelyi, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/530,028

(22) Filed: Jun. 21, 2012

(65) Prior Publication Data
US 2012/0258144 A1 Oct. 11, 2012

Related U.S. Application Data

(60) Continuation of application No. 12/395,539, filed on Feb. 27, 2009, now Pat. No. 8,227,438, which is a division of application No. 10/489,839, filed as application No. PCT/US02/30532 on Sep. 24, 2002, now Pat. No. 7,514,414.

(60) Provisional application No. 60/324,484, filed on Sep. 24, 2001, provisional application No. 60/400,826, filed on Aug. 1, 2002.

(51) Int. Cl.
A61K 31/70 (2006.01)

(52) U.S. Cl.
USPC ........ 536/24.3; 536/24.5; 536/23.1; 536/25.6

(58) Field of Classification Search
None
See application file for complete search history.

(56) References Cited

U.S. PATENT DOCUMENTS

| 4,469,863 | A | 9/1984 | Ts'o et al. | |
|---|---|---|---|---|
| 5,023,243 | A | 6/1991 | Tullis | |
| 5,643,890 | A | 7/1997 | Iversen et al. | |
| 5,663,153 | A | 9/1997 | Hutcherson et al. | |
| 5,837,729 | A | 11/1998 | Bourinbaiar | |
| 6,214,806 | B1 | 4/2001 | Krieg et al. | |
| 6,288,042 | B1 | 9/2001 | Rando et al. | |
| 7,094,766 | B1 | 8/2006 | Gilchrest et al. | |
| 7,514,414 | B2 | 4/2009 | Klinman et al. | |
| 7,514,415 | B2 * | 4/2009 | Klinman et al. | 514/44 R |
| 7,951,786 | B2 * | 5/2011 | Klinman et al. | 514/44 A |
| 8,043,622 | B2 * | 10/2011 | Klinman et al. | 424/184.1 |
| 8,053,422 | B2 * | 11/2011 | Klinman et al. | 514/44 R |
| 2003/0087848 | A1 | 5/2003 | Bratzler et al. | |
| 2004/0132682 | A1 | 7/2004 | Klinman et al. | |
| 2004/0248834 | A1 | 12/2004 | Klinman et al. | |
| 2006/0074039 | A1 | 4/2006 | Klinman et al. | |
| 2009/0082288 | A1 | 3/2009 | Klinman et al. | |
| 2009/0142310 | A1 | 6/2009 | Klinman et al. | |
| 2009/0208468 | A1 | 8/2009 | Klinman et al. | |
| 2010/0144839 | A1 | 6/2010 | Klinman et al. | |
| 2011/0077289 | A1 | 3/2011 | Klinman et al. | |

FOREIGN PATENT DOCUMENTS

| EP | 0 092 574 | 4/1992 |
|---|---|---|
| EP | 1 167 377 | 1/2002 |
| WO | WO 83/01451 | 4/1983 |
| WO | WO 93/23572 | 11/1993 |
| WO | WO 95/26204 | 9/1995 |
| WO | WO 96/02555 | 2/1996 |
| WO | WO 98/11211 | 3/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 99/51259 | 10/1999 |
| WO | WO 03/027313 | 4/2003 |
| WO | WO 2004/012669 | 2/2004 |

OTHER PUBLICATIONS

Balagurummorthy et al., "Hairpin and parallel quartet structure for telomeric sequences," *Nucleic Acids Res.* 20(15):4061-4067 (Aug. 1992).
Battegay, "Angiogenesis: mechanistic insights, neovascular diseases, and therapeutic prospects," *J. Molec. Med.* 73(7): 333-346, (1995).
Beck and D'Amore, "Vascular development: cellular and molecular regulation," *FASEB J.* 11(5): 365, (1997).
Bjersing et al., "Anti-proliferative effects of phosphodiester oligodeoxynucleotides," *Immunobiology*, 209(8):637-45, (2004).
Braun et al., "On the difficulties of establishing a consensus on the definition of and diagnostic investigations for reactive arthritis," *J. Rheumatol.*, 27:2185-2192, (2000).
Britigan et al., "Lactoferrin Binds CpG-Containing Oligonucleotides and Inhibits Their Immunostimulatory Effects on Human B Cells," *J. Immunol.* 167:2921-2928, (2001).
Chatziantoniou, "Telomerase: biological function and potential role in cancer management," *Pathology Oncology Research*, 7(3): 161-170, (2001).
Chen et al., "Identification of methylated CpG motifs as inhibitors of the immune stimulatory CpG motifs," *Gene Ther.*, 8(13):1024-1032, (2001).
Deng et al., "Synovial cytokine mRNA expression during arthritis triggered by CpG motifs of bacterial DNA," *Arthritis Res,.* 3:48-53, (2001).

(Continued)

*Primary Examiner* — Michelle S Horning
(74) *Attorney, Agent, or Firm* — Klarquist Sparkman, LLP

(57) ABSTRACT

The present disclosure relates to oligodeoxynucleotides that suppress an immune response. Methods are disclosed for preventing or treating an immune-mediated disorder, such as, but not limited to, an autoimmune disease, by administering a therapeutically effective amount of a suppressive oligodeoxynucleotide. Also disclosed are methods of suppressing an immune response in a subject by administering a therapeutically effective amount of a suppressive oligodeoxynucleotide.

18 Claims, 19 Drawing Sheets

(56) References Cited

OTHER PUBLICATIONS

Deng et al., "The features of arthritis induced by CpG motifs in bacterial DNA," *Arthritis Rheum.*, 43:356-364, (2000).
Deng et al., "Intra-articularly localized bacterial DNA containing CpG motifs induces arthritis," *Nat. Med.*, 5:702-705, (1999).
Dong et al., "Suppressive Oligodeoxynucleotides Delay the Onset of Glomerulonephritis and Prolong Survival in Lupus-Prone NZB X NZW Mice," *Arthritis & Rheumatism* 52(2):651-658 (Feb. 2005).
Dong et al., "Suppressive Oligonucleotides Protect Against Collagen-Induced Arthritis in Mice," *Arthritis & Rheumatism* 50(5):1686-1689 (May 2004).
Enokizono et al., "Structure of hnRNP D Complexed with Single-stranded Telomere DNA and Unfolding of the Quadruplex by Heterogeneous Nuclear Ribonucleoprotein D," *J. Biological Chemistry* 280(19):18862-18870 (2005).
Gaudric et al,. "Quantification of angiogenesis due to basic fibroblast growth factor in a modified rabbit corneal model," *Ophthal.* Res. 24: 181, (1992).
Goldenberg et al., "Arthritis in rabbits induced by killed *Neisseria gonorrhoeae* and gonococcal lipopolysaccharide," *J. Rheumatol* (Abstract), 11(1): 3-8, (1984).
Gursel et al., "Repetitive Elements in Mammalian Telomeres Suppress Bacterial DNA-Induced Immune Activation," *J. Immunology* 171:1393-1400 (2003).
Gursel, I., et al., ",,Sterically stabilized cationic liposomes improve the uptake and immunostimulatory activity of CpG oligonucleotides, *J. Immunol.* 167(6): 3324-3328, (2001).
Gursel, M., et al., "Differential and competitive activation of human immune cells by distinct classes of CpG oligodeoxynucleotide," *J.Leuko.Biol.* 71:813-820, (2002).
Han & Hurley, "G-quadruplex DNA: a potential target for anti-cancer drug design," *Trends Pharmacol. Sci.* 21:136-142, (2000).
Hartmann et al., "CpG DNA: a potent signal for growth, activation, and maturation of human dendritic cells," *Proc. Natl. Acad. Sci. USA* 96:9305-9310, (1999).
Ho et al., "An Immunomodulatory GpG Oligonucleotide for the Treatment of Autoimmunity via the Innate and Adaptive Immune Systems," *J. Immunol.* 171:4920-4926, (2003).
International Search Report from the prior PCT Application No. PCT Application No. PCT/US02/30532, 3 pages, (mailed on Jun. 30, 2003).
Iwakura et al., "The development of autoimmune inflammatory arthropathy in mice transgenic for the human T cell leukemia virus type-1 env-pX region is not dependent on H-2 haplotypes and modified by the expression levels of Fas antigen," *J. of Immunology*, 161:6592-6598 (1998).
Jing, "Developing G-quartet oligonucleotides as novel anti-HIV agents: focus on anti-HIV drug design," *Investig. Drugs*. 9(8):1777-1785 (Aug. 2000).
Kenyon et al., "A model of angiogenesis in the mouse cornea," *Invest Opthalmol. Vis. Sci.* 37:1625-1632, (1996).
Klinman et al., "Activation of the innate immune system by CpG oligodeoxynucleotides: immunoprotective activity and safety," *Springer Semin. Immunopathol.* 22:173-83, (2000).
Klinman et al., "Contribution of CpG motifs to the immunogenicity of DNA vaccines," *J.Immunol.* 158:3635-3639, (1997).
Klinman et al., "CpG motifs present in bacteria DNA rapidly induce lymphocytes to secrete interleukin 6, interleukin 12, and interferon gamma," *Proc. Natl. Acad. Sci. USA* 93: 2879, (1996).
Krieg et al., "CpG motifs in bacterial DNA trigger direct B-cell activation," *Nature* 374: 546, (1995).
Krieg et al., "Enhancing vaccines with immune stimulatory CpG DNA," *Curr Opin Mol Ther* 3(1):15-24, (2001).
Krieg et al., "Sequence motifs in adenoviral DNA block immune activation by stimulatory CpG motifs," *Proc. Natl. Acad. Sci. USA* 95:12631-12636, (1998).
Krieg, "Commentary: A possible cause of joint destruction in septic arthritis," *Arthritis Research* 1(1):3-4, (1999).
Krieg, "CpG Motifs in bacterial DNA and their immune effects," *Annu Rev Immunol* 20:709-760, (2002).
Krieg, "From A to Z on CpG," *Trends Immunol.* 23(2):64-65, (2002).
Krieg, "From bugs to drugs: therapeutic immunomodulation with oligodeoxynucleotides containing CpG sequences from bacterial DNA," *Antisense Nucleic Acid Drug Dev* 11(3):181-188; (2001).
Lenert et al., "CpG stimulation of primary mouse B cells is blocked by inhibitory oligodeoxyribonucleotides at a site proximal to NF-kappaB activation," *Antisense Nucleic Acid Drug Dev.* 11, 247-256, (2001).
Liang et al., "Activation of human B cells by phosphorothioate oligodeoxynucleotides," *J. Clin. Invest.* 98:1119-1129, (1996).
Lichtenberg et al., "The Rat Subcutaneous Air Sac Model: A Quantitative Assay of Antiangiogenesis in Induced Vessels," *Pharmacol Toxicol.* 84: 34, (1999).
Murchie & Lilley, "Tetraplex folding of telomere sequences and the inclusion of adenine bases," *EMBO J.* 13:993-1001, (1994).
Pisetsky et al., "Immunological properties of bacterial DNA," *NY Acad. Sci.* 772:152, (1995).
Pisetsky et al., "Inhibition of murine macrophage IL-12 production by natural and synthetic DNA," *Clin. Immunol.* 96, 198-204, (2000).
Quarcoo et al., "Inhibition of signal transducer and activator of transcription 1 attenuates allergen-induced airway inflammation and hyperreactivity," *J Allergy Clin Immunol.*, 114(2):288-95, (2004).
Roman, M., et al., "Immunostimulatory DNA sequences function as T helper-1-promoting adjuvants," *Nature Medicine* 3:849, (1997).
Schwartz et al., "Bacterial DNA or Oligonucleotides Containing Unmethylated CpG Motifs Can Minimize Lipopolysacchraide-Induced Inflammation in the Lower Respiratory Tract Through an IL-12-Dependent Pathway," *J. Immunol.* 163:224-231, (1999).
Schwartz et al., CpG Motifs in Bacterial DNA Cause Inflammation in the Lower Respiratory Tract, *J. Clin. Invest.* 100:68-73, (1997).
Shirota et al., "Suppressive Oligodeoxynucleotides Protect Mice from Lethal Endotoxic Shock," *J. Immunology* 174:4579-4583, (2005).
Stunz et al., "Inhibitory oligonucleotides specifically block effects of stimulatory CpG oligonucleotides in B cells," *Eur. J. Immunol.* 32:1212-1222, (2002).
Verthelyi et al., "Human peripheral blood cells differentially recognize and respond to two distinct CPG motifs," *J. Immunol.* 166:2372-2377, (2001).
Vialas et al., "Oxidative damage generated by an oxo-metalloporphyrin onto the human telomeric sequence," *Biochemistry* 39:9514-9522, (2000).
Williamson, "G-quartets in biology: reprise," *PNAS*, 90:3124, (1993).
Wilting et al., "A modified chorioallantoic membrane (CAM) assay for qualitative and quantitative study of growth factors. Studies on the effects of carriers, PBS, angiogenin, and bFGF," *Anat. Embryol.* 183: 259, (1991).
Yamada et al., "Effect of suppressive DNA on CpG-induced immune activation," *J. Immunol.* 169:5590-5594, (2002).
Yamamoto et al., "Unique palindromic sequences in synthetic oligonucleotides are required to induce IFN and augment ING-mediated natural killer cells activity," *J. Immunol.* 148:4072, (1992).
Yi et al., "CpG motifs in bavterial DNA: systemic induction of IL-6transcription through an anti-oxidant sensitive pathway," *J. Immun.* 157: 5394-5402, (1996).
Yoshino and Ohsawa, "The role of lipopolysaccharide injected systemically in the reactivation of collagen-induced arthritis in mice," *British Journal of Pharmacology* 129:1309-1314 (2000).
Zeuner et al., "Reduction of CpG-induced arthritis by suppressive oligodeoxynucleotides," *Arthritis & Rheumatism* 46(8):2219-2224, (2002).
Zhao et al., "Requirements for effective inhibition of immunostimulatory CpG motifs by neutralizing motifs," *Antisense Nucleic Acid Drug Dev.* 10(5):381-389, (2000).
Zheng et al., "DNA containing CpG motifs induces angiogenesis," *PNAS* 99(13):8944-8949, (2002).
Bernard, "Acute respiratory distress syndrome: a historical perspective," *J. Respir. Crit. Care Med*. 172(7):798-806 (2005).
Brodie et al, "Immunostimulatory DNA sequences inhibit IL-5, eosinophilic inflammation, and airway hyperresponsiveness in mice," *J Immunol.* 161:7054-7062 (1998).

(56) References Cited

OTHER PUBLICATIONS

Burt et al., "Treatment of Autoimmune Disease by Intense Immunosuppressive Conditioning and Autologous Hematopoietic Stem Cell Transplantation," Blood 92(10):3505-3514 (Nov. 1998).
Goldberg et al., "Beyond danger: Unmethylated CpG dinucleotides and the immunopathogenesis of disease," *Immunol. Lett.* 73:13-18 (2000).
Heeg and Zimmermann, "CpG DNA as a Th1 trigger," *Int. Arch. Allergy Immunol.* 121:87-97 (2000).
International Search Report from the prior PCT Application No. PCT Application No. PCT/US2003/024205, 3 pages (mailed on Nov. 18, 2005).
Klinman et al, "Mice from Lethal Endotoxic Shock Suppressive Oligodeoxynucleotides Protect," Journal of Immunology 174:4579-4583 (2005).
Klinman et al, "Synthetic oligonucleotides as modulators of inflammation," *J. Leukocyte Biol.* 84:958-964 (2008).
Matsukawa et al., "Production of IL-1 and IL-1 receptor antagonist and the pathological significance in lipopolysaccharide-induced arthritis in rabbits," *Clin. Exp. Immunol.*, 93(2):206-211 (1993).
Matthay et al., "Future research directions in acute lung injury: Summary of a National Heart, Lung, and Blood Institute working group," *Am. J Respir. Crit. Care Med* .167:1027-1035 (2003).
McCluskie et al., "Psarental and Mucosal Prime-boost Immunization Strategies in Mice with Hepatitis B Surface Antigen and CpG DNA," *FEMS Immunology and Medical Microbiology* 32:179-185 (2002).
Sato et al., "Suppressive Oligodeoxynucleotides Inhibit Silica-Induced Pulmonary Inflammation," *J. Immunol.* 180:7648-7654 (2008).
Schnitzer and Hochberg, "cox-2-Selective Inhibitors in the treatment of Arthritis," *Cleveland Clinic Journal of Medicine* 69(1): SI-20-30 (Apr. 2002).
van der Vliet, "Nitric oxide: A pro-inflamatory mediator in lung disease?," *Respir. Res.* 1:67-72 (2000).
Yamada et al., "Suppressive oligodeoxynucleotides inhibit CpG-induced inflammation of the mouse lung," *Crit. Care Med.* 32(1): 2045-2049 (2004).
Zeuner et al., "Influence of Stimulatory and Suppressive DNA Motifs on Host Susceptibility to Inflammatory Arthritis," Arthritis and Rheumatism, 48(6):1701-1707, (Jun. 2003).

* cited by examiner

G-tetrad

Quadruplex

GG base pair

Hairpin

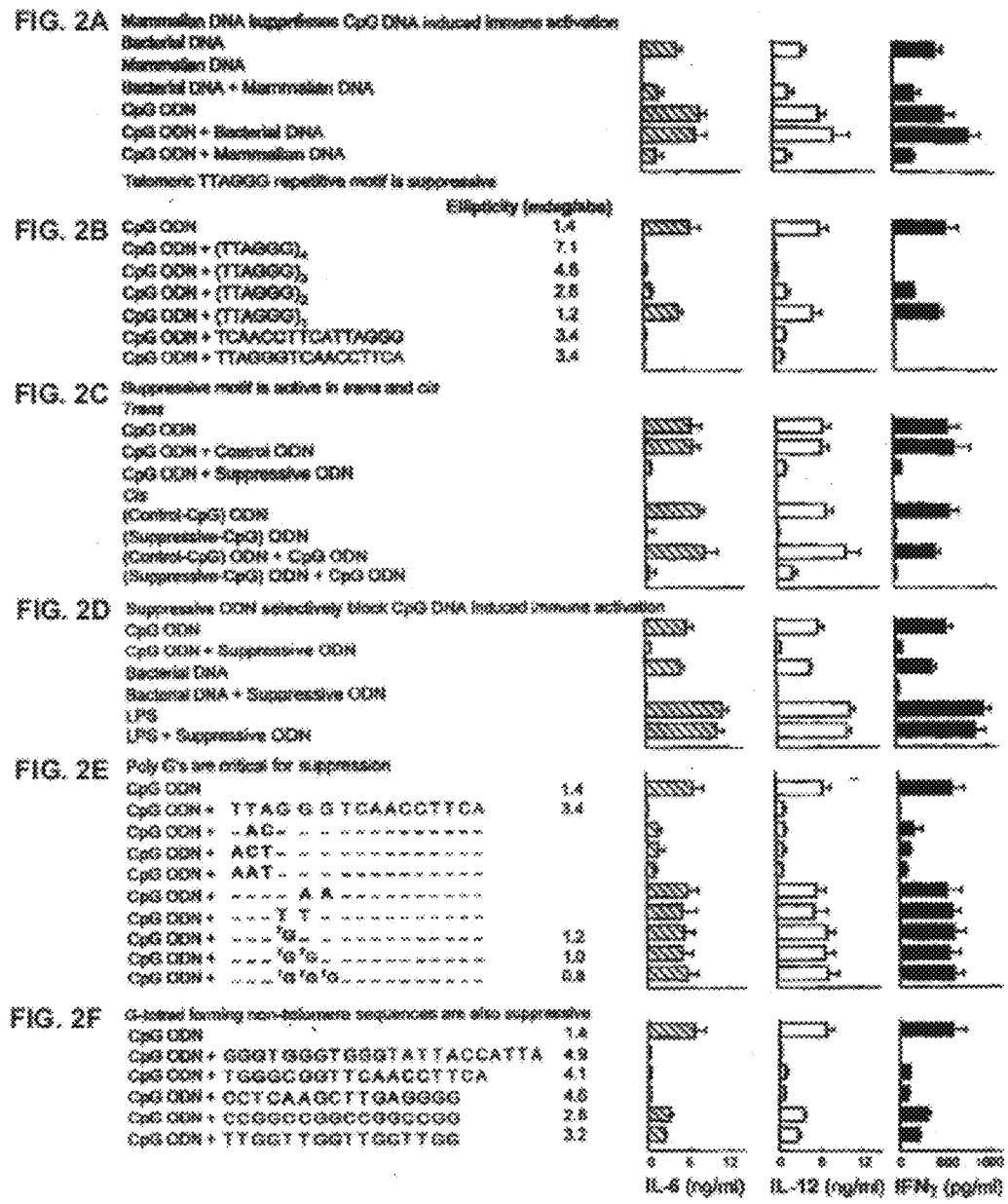

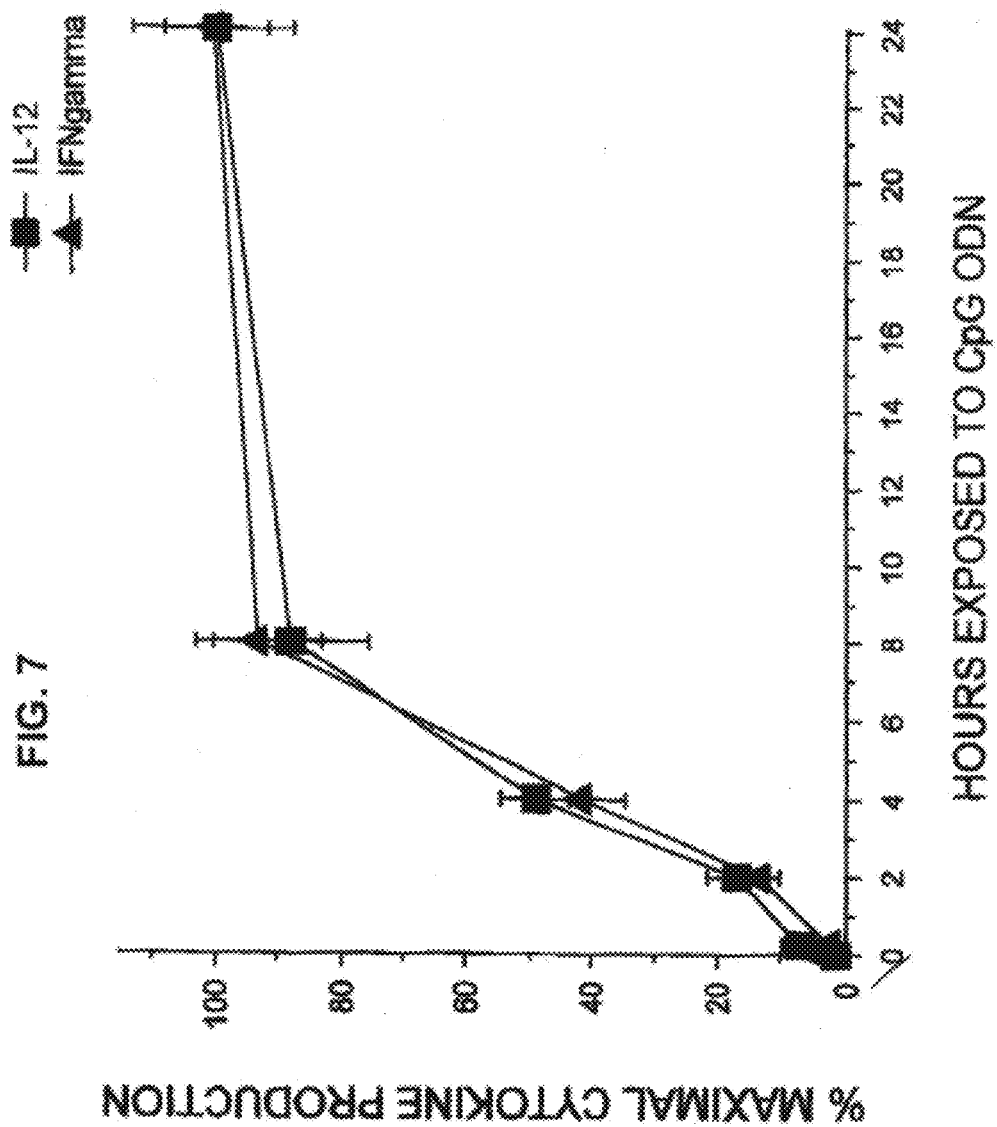

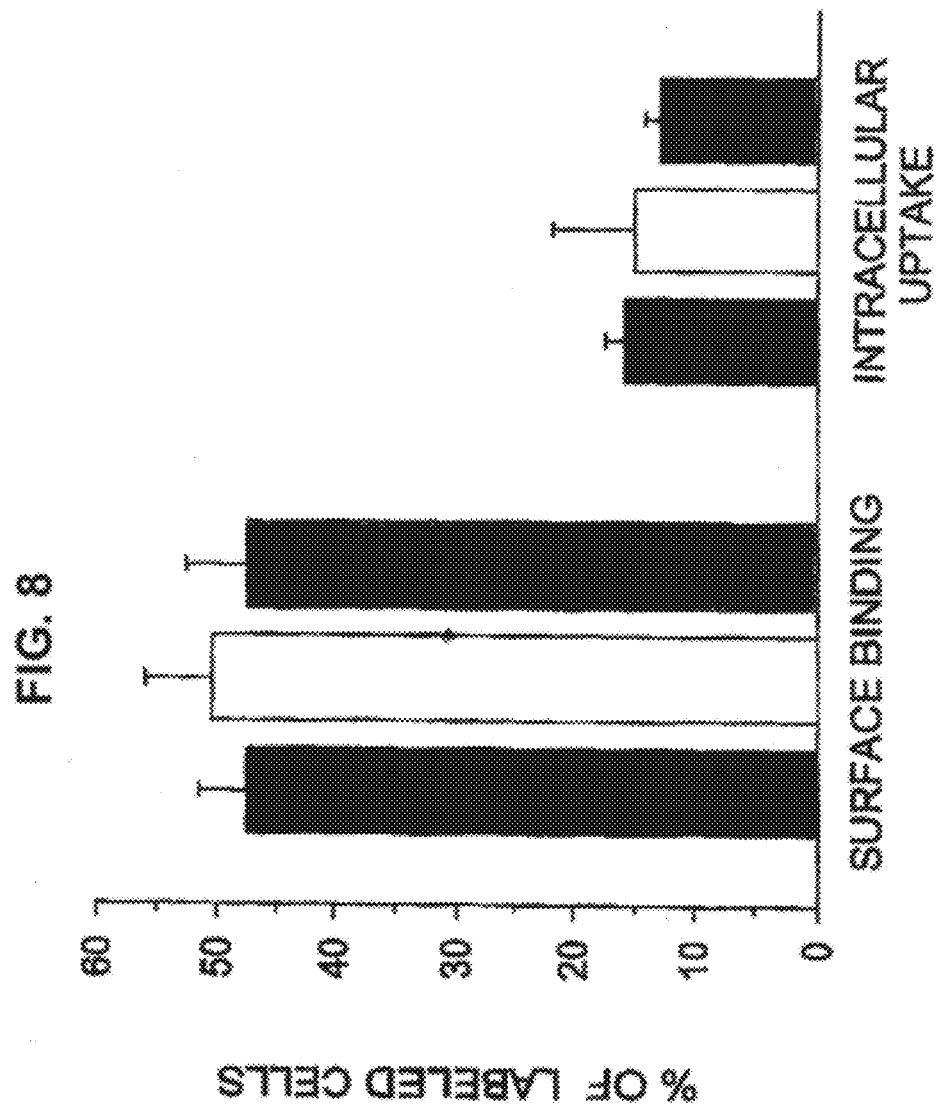

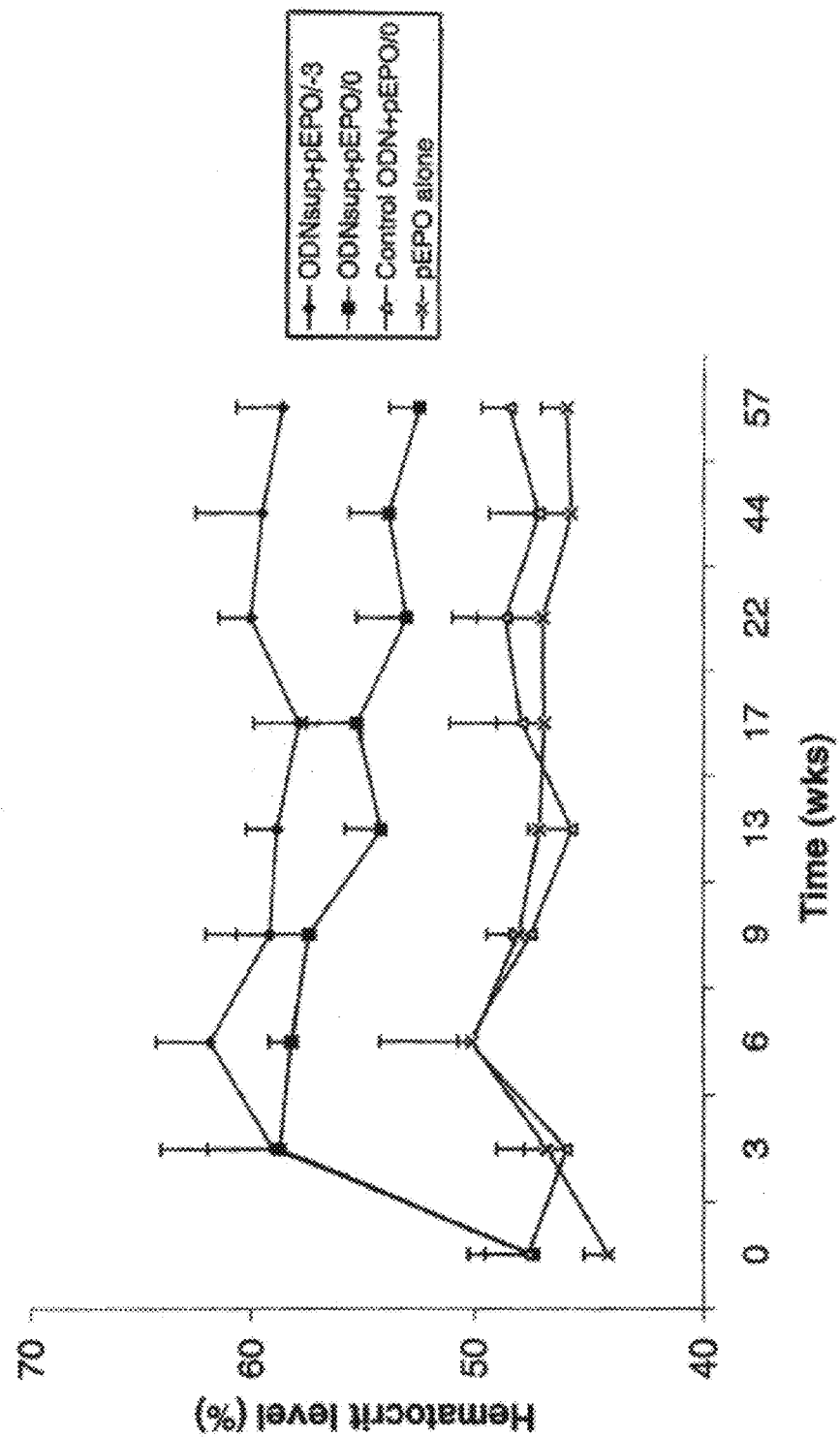

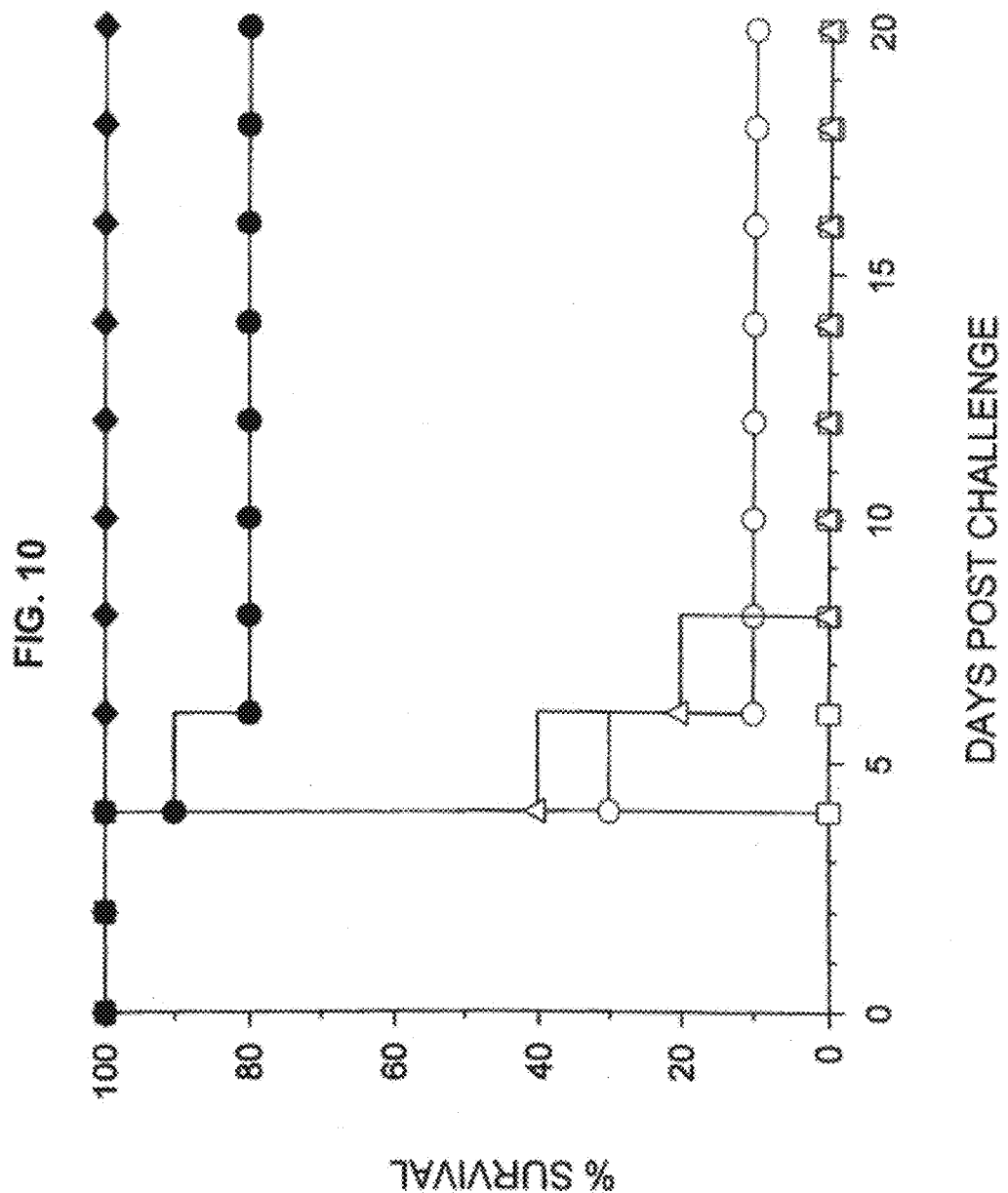

US 8,580,944 B2

SUPPRESSORS OF CPG OLIGONUCLEOTIDES AND METHODS OF USE

PRIORITY CLAIM

This is a continuation of U.S. application Ser. No. 12/395,539, filed on Feb. 27, 2009 now U.S. Pat. No. 8,227,438, which is a divisional of U.S. application Ser. No. 10/489,839, filed on Mar. 16, 2004 now U.S. Pat. No. 7,514,414, which is the §371 U.S. National Stage of International Application No. P0CT/US02/30532, filed on Sep. 24, 2002, which was published in English under PCT Article 21(2), which in turn claims the benefit of U.S. Provisional Patent Application No. 60/324,484, filed on Sep. 24, 2001, and U.S. Provisional Patent Application No. 60/400,826, filed on Aug. 1, 2002. All of the prior applications are incorporated by reference herein in their entirety.

FIELD OF THE DISCLOSURE

The present disclosure relates to oligodeoxynucleotides that suppress an immune response, and to methods of using these oligonucleotides to treat disorders associated with an immune response.

BACKGROUND

The immune system is composed of many interdependent cell types that collectively protect the body from bacterial, parasitic, fungal, viral infections and from the growth of tumor cells. Many of these cell types, such a B cells, macrophages, an Natural Killer cells, have specialized functions. The cells of the immune system can engulf bacteria, kill parasites or tumor cells, or kill viral-infected cells. Often, these cells depend on the T helper subset for activation signals in the form of secretions formally known as cytokines, lymphokines, or more specifically interleukins.

Cells of the immune system recognize and are activated by conserved pathogen associated molecular patterns (PAMPs) in infectious agents. The unmethylated CpG dimers embedded in bacterial DNA, as well as certain synthetic oligodeoxynucleotides (ODNs) containing unmethylated CpG sequences (termed a CpG motif) that emulated them, are more frequent in the genomes of bacteria and viruses than vertebrates. Recent studies suggest that immune recognition of these motifs may contribute to the host's innate immune response (Klinman et al., *Proc. Natl. Acad. Sci. USA* 93: 2879, 1996; Yi et al., *J. Immun.* 157: 5394, 1996; Liang et al., *J. Clin. Invest.* 98:1119, 1996; Krieg et al., *Nature* 374: 546, 1995).

In mice, CpG DNA induces proliferation in almost all (>95%) of B cells and increases immunoglobulin (Ig) secretion. This B-cell activation by CpG DNA is T-cell independent and antigen non-specific. In addition to its direct effects on B cells, CpG DNA has also been shown to activate cells of the immune system (see, for example, International Patent Applications WO 95/26204, WO 96/02555, WO 98/11211, WO 98/18810, WO 98/37919, WO 98/40100, WO 98/52581, PCT/US98/047703, and PCT/US99/07335; U.S. Pat. No. 5,663,153).

However, in many situations, there is a need to suppress an immune response. For example, in an autoimmune disease, a foreign antigen mimics one or more self-proteins, and the immune system produces a response in which a tissue is consequently injured. Similarly, when a subject is the recipient of a transplanted tissue (e.g. a heart, lung, pancreas, or kidney recipient), the body can produce an immune response against the donor tissue. In this situation, there is a clear need to suppress the immune response, in order to avoid rejection of the graft. Additionally, there is a need to suppress the immune response in order to prevent or treat allergic disorders such as asthma.

In view of the above, there exists a need for agents that suppress immune responses. Specifically, there is a need for agents that can be used to suppress the inflammation, and that can be used to suppress an the immune response associated with autoimmune diseases, allergies, and transplant rejection.

BRIEF SUMMARY OF SPECIFIC EMBODIMENTS

Oligodeoxynucleotides are disclosed herein that can be used to suppress immune activation. These suppressive oligodeoxynucleotides are of use in preventing and/or treating a variety of diseases and disorders that include, but are not limited to, autoimmune diseases. Specific, non-limiting examples of autoimmune disorders are inflammatory arthritis, Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave.s disease, among others. The suppressive oligodeoxynucleotides can be administered locally, such as, but not limited to, administration by intra-articular injection or inhalation, or can be administered systemically.

A substantially pure or isolated oligodeoxynucleotide (ODN) is disclosed herein that is at least about 8 nucleotides in length, forms a G tetrad, has a CD value of greater than 2.9, has at least two guanosines, and suppresses an immune response. Optionally, the suppressive ODN has multiple guanosine-rich sequences, and in some examples, the ODN has one or more TTAGGG motifs. Furthermore, in particular embodiments, the ODN is modified to prevent degradation or is part of an oligodeoxynucleotide delivery complex that includes a targeting moiety. In one specific, non-limiting example the suppressive ODN suppresses CpG-DNA-induced immune activation.

Also disclosed herein is a pharmacological composition that includes the suppressive ODN and a pharmacologically acceptable carrier.

In another embodiment, a method is disclosed for treating or preventing an autoimmune disease in a subject. The method includes administering a therapeutically effective amount of the suppressive ODN to a subject having or at risk of developing an autoimmune disease, thereby treating or preventing the autoimmune disease. In some embodiments, the ODN is administered orally, intravenously, intra-muscularly, sub-cutaneously, or intra-articularly.

In another embodiment, a method is disclosed for treating or preventing an autoimmune disease in a subject that includes contacting immune cells with the suppressive ODN in vitro. The immune cells are and transferred to a subject having or at risk of developing an autoimmune disease.

Other embodiments are methods of suppressing an immune response in a subject including administering a therapeutically effective amount of a suppressive ODN to a subject in which it is desirable to suppress an immune response, thereby suppressing the immune response.

Also described herein is a kit for treating or preventing an autoimmune disease in a subject that includes the suppressive ODN and instructions for administering the ODN to a subject.

BRIEF DESCRIPTION OF THE FIGURES

FIG. 1: is a set of diagrams of the structure of a G-tetrad.

FIG. 2: is a set of graphs showing the factors contributing to the suppression of CpG-induced immune activation. FIG. 2A is a graph showing that mammalian DNA suppresses CpG DNA-induced immune activation. FIG. 2B is a graph showing that the telomeric TTAGGG repetitive motif is suppressive. FIG. 2C is a graph showing that the suppressive motif is active in trans and cis conformations.

FIG. 2D is a graph showing that suppressive ODNs selectively block CpG DNA-induced immune activation. FIG. 2E is a graph showing that Poly Gs are critical for suppression. FIG. 2F is a graph showing that G-tetrad forming non-telomere sequences are also suppressive.

FIG. 3: is a pair of graphs showing that G-tetrad-forming suppressive ODNs selectively suppress CpG-induced immune activation.

FIG. 7: is a graph showing the effect of removing CpG ODN from cultured cells. 1 μM of CpG ODN1555 was added to BALB/c spleen cells at T=0. The cells were washed free of this ODN after various incubation periods. IFNγ and IL-12 levels in culture supernatants were measured by ELISA after 24 h. Results represent the average+SD of duplicate cultures. Similar results were obtained in studies of CpG ODN1466.

FIG. 8: is a graph showing that suppressive ODN do not block the binding or uptake of CpG ODN. BALB/c spleen cells were incubated with 1 μM of CpG ODN1555 (black bar) plus 1 μM of suppressive ODN1502 (grey bar) or control ODN1612 (white bar). The percent of cells that bound or internalized the CpG ODN was determined by FACS. Similar results were obtained using CpG ODN1466, suppressive ODNH154 and control ODN1471.

FIG. 9: is a graph showing that suppressive ODN permit higher levels of transgene expression.

FIG. 10: is a graph showing that suppressive ODN blocks the activity of CpG motifs in vivo.

FIG. 11: is a set of graphs showing the effect of CpG ODN and suppressive ODN injection into the knee.

FIG. 13: is a set of graphs that demonstrate that administration of suppressive ODN decreases TNFα upregulation following CpG ODN injection.

BRIEF DESCRIPTION OF THE SEQUENCE LISTING

Figure 1A:
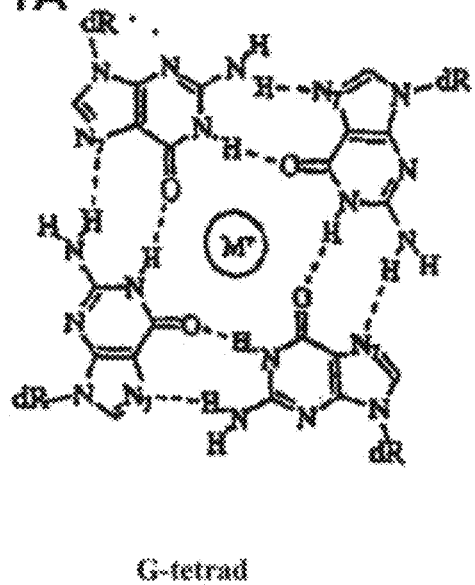
FIG. 1A is a diagram of the structure of an individual G-tetrad that shows the Hoogsteen base pairing. M⁺ represents a monovalent cation such as K⁺ or Na⁺ and dR is the sugar-phosphate backbone.
Figure 1B:
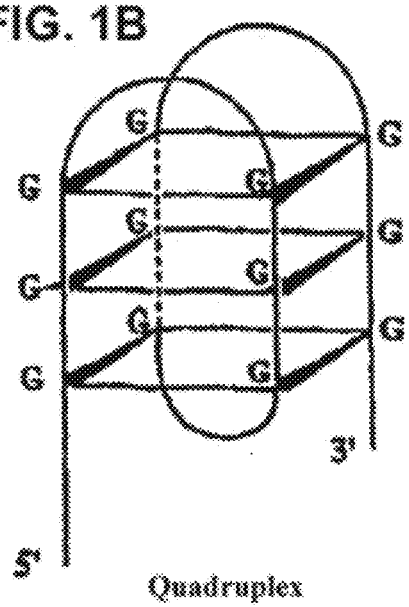
FIG. 1B is a schematic representation showing the possible folded intramolecular quadruplex structure.
Figure 1C:
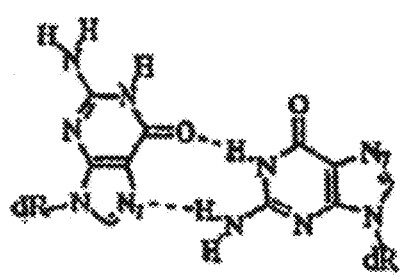
FIG. 1C is a schematic showing the GG-base pair formed by means of Hoogsteen hydrogen bonds.
Figure 1D:
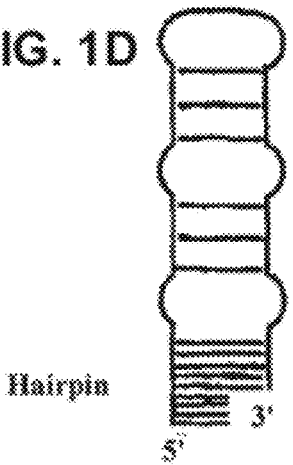
FIG. 1D is a schematic of an intramolecular hairpin.

The Sequence Listing is submitted as an ASCII text file [4239-67747-03_Sequence_Listing.txt, Jun. 21, 2012, 6.74 KB], which is incorporated by reference herein.

SEQ ID NOs 1-25 are suppressive ODN sequences.
SEQ ID NOs 28, 29, and 31 are control ODN sequences.
SEQ ID NOs 26, 27, and 30 are immunostimulatory CpG sequences.

DETAILED DESCRIPTION OF SEVERAL EMBODIMENTS

I. Abbreviations
A: adenine
Ab: antibody
C: cytosine
CD: circular dichroism
CpG ODN: an oligodeoxynucleotide including a CpG motif.
DC: dendritic cell
FCS: fetal calf serum
G: guanine
GI: gastrointestinal
GU: genitourinary
h: hour
IFN-α: interferon alpha
IFN-γ: interferon gamma
IL-10: interleukin 10
mm: millimeter
mRNA: messenger ribonucleic acid.
ODN: oligodeoxynucleotide
Pu: purine
Py: pyrimidine
s.c.: subcutaneous
T: thymine
µg: microgram II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Allergy: An example of an immune-mediated disorder. An allergy is a collection of symptoms caused by an exaggerated immune response or reaction to substances that do not trigger an immune response in most people. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions which could be provoked by many antigens. In practice these types do not necessarily occur in isolation from each other.

Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms.

Animal: Living multi-cellular vertebrate organisms, a category that includes, for example, mammals and birds. The term mammal includes both human and non-human mammals. Similarly, the term "subject" includes both human and veterinary subjects.

Angiogenesis: A process leading to the generation of new blood vessels through sprouting from already existing blood vessels. The process involves the migration and proliferation of endothelial cells from preexisting vessels. Angiogenesis occurs both during pre-natal development, post-natal development, and in the adult. In the adult angiogenesis occurs during the normal cycle of the female reproductive system, wound healing, and during pathological processes such as cancer (for review see Battegay, *J. Molec. Med.* 73(7): 333-346, 1995; Beck and D'Amore, *FASEB J.* 11(5): 365, 1997)

Angiogenic Factor: A molecule that promotes angiogenesis. A plethora of experiments have suggested that tissues secrete factors which promote angiogenesis under conditions of poor blood supply during normal and pathological angiogenesis processes. Angiogenic molecules are generated by tumor, inflammatory, and connective tissue cells in response to hypoxia and other as-yet ill-defined stimuli. The first indication of the existence of such diffusible substances was gleaned from filtration experiments demonstrating that tumor cells separated from underlying tissues by filters that do not allow passage of cells are nevertheless capable of supporting vessel growth in these tissues. The formation of blood vessels is initiated and maintained by a variety of factors secreted either by the tumor cells themselves or by accessory cells. Many different growth factors and cytokines have been shown to exert chemotactic, mitogenic, modulatory or inhibitory activities on endothelial cells, smooth muscle cell and fibroblasts and can, therefore, be expected to participate in an angiogenic process in one way or another. For example, factors modulating growth, chemotactic behavior and/or functional activities of vascular endothelial cells include αFGF, βFGF, angigiogenein, angiotropin, epithelial growth factor, IL-8, and vascular endothelial growth factor (VEGF), amongst others.

As many angiogenic factors are mitogenic and chemotactic for endothelial cells their biological activities can be determined in vitro by measuring the induced migration of endothelial cells or the effect of these factor on endothelial cell proliferation. Alternatively, a bioassay may be utilized for direct determination of angiogenic activities and permit repeated, long-term quantitation of angiogenesis as well as physiological characterization of angiogenic vessels. Many such assays are known in the art.

One assay employs the use of a non-vascularized mouse eye (e.g. Kenyon et al., *Invest Opthalmol. Vis. Sci.* 37:1625, 1996; also see Examples section) or the rabbit eye (e.g., see Gaudric et al., *Ophthal. Res.* 24: 181, 1992), and is termed a cornea pocket assay. This assay has the advantage that new blood vessels are easily detected and essentially must be newly formed blood vessels in the normally avascular cornea. Another assay involves the use of chicken chorioallantoic membrane (the CAM assay; see Wilting et al., *Anat. Embryol.* 183: 259, 1991). Other assays in the rat, such as the rat aortic ring model, provide reproducible assays that are often utilized to identify angiogenic agonists and antagonists (e.g. see Lichtenberg et al., *Pharmacol Toxicol.* 84: 34, 1999).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

Arthritis: Arthritis is an inflammatory disease that affects the synovial membranes of one or more joints in the body. It is the most common type of joint disease, and it is characterized by the inflammation of the joint. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

One type of arthritis is reactive arthritis, which is an acute nonpurulent arthritis secondary to a urinary tract or gastrointestinal infection with a variety of microorganisms, including *Chlamydia trachomatis, Yersinia, Salmonella, Shigella*, and *Campylobacter*. Microbial components are found in the affected joints. The arthritis appears abruptly and tends to involve the knees and ankles, but sometimes involves the wrists, fingers, and/or toes. Untreated, the arthritis lasts for about a year, then generally abates and only rarely is accompanied by ankylosing spondylitis. Despite evidence of disease being triggered by bacterial infection, viable bacteria are rarely present in affected joints and antibiotic treatment seldom provides relief.

Another type of arthritis is rheumatoid arthritis. Rheumatoid arthritis is a chronic, systemic, inflammatory disease that affects the synovial membranes of multiple joints in the body. Because the disease is systemic, there are many extra-articular features of the disease as well. For example, neuropathy, scleritis, lymphadenopathy, pericarditis, splenomegaly, arteritis, and rheumatoid nodules are frequent components of the disease. In most cases of rheumatoid arthritis, the subject has remissions and exacerbations of the symptoms. Rheumatoid arthritis considered an autoimmune disease that is acquired and in which genetic factors appear to play a role.

Autoimmune disorder: A disorder in which the immune system produces an immune response (e.g., a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave.s disease, among others.

CD value: The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. The higher the ellipticity value, the greater the tetrad-forming capacity of the oligonucleotide.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligodeoxynucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cytokine: Proteins made by cells that affect the behavior of other cells, such as lymphocytes. In one embodiment, a cytokine is a chemokine, a molecule that affects cellular trafficking.

Epitope: An antigenic determinant. These are particular chemical groups or peptide sequences on a molecule that are antigenic, i.e., that elicit a specific immune response. An antibody binds a particular antigenic epitope.

Functionally Equivalent Sequence alterations, for example in a suppressive ODN, that yield the same results as described herein. Such sequence alterations can include, but are not limited to, deletions, base modifications, mutations, labeling, and insertions.

Graft-versus-host disease: Tissue rejection, also called graft-versus-host disease, is a consequence of organ or tissue transplantation caused by the transplant recipient's (host's) immune response to the transplanted organ/tissue which can damage or destroy it. Ordinarily, the immune response protects the body from potentially harmful substances (antigens) such as microorganisms, toxins, and cancer cells. The immune system distinguishes "self" from "foreign" by reacting to proteins on the surfaces of cells. It reacts against substances it recognizes as foreign (antigens). The presence of foreign blood or tissue in the body triggers an immune response that can result in blood transfusion reactions and transplant rejection when antibodies are formed against foreign antigens on the transplanted or transfused material.

G-tetrad: G-tetrads are G-rich DNA segments that can accommodate complex secondary and/or tertiary structures (see FIG. 1). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values.

Oligonucleotides that form G-tetrads can also form higher-level aggregates that are more easily recognized and taken up by immune cells, for example, through scavenger receptors or by nucleolin.

Guanosine-rich sequence: A hexameric region of a nucleotide sequence in which >50% of the bases are Gs.

Immunostimulatory CpG ODN: An oligodeoxynucleotide, which contains a cytosine, guanine dinucleotide sequence and stimulates (e.g., has a mitogenic effect) vertebrate immune cells. The cytosine, guanine is unmethylated. Both D and K type CpG ODNs are immunostimulatory (see in Verthelyi et al., J. Immunol. 166:2372-2377, 2001, which is herein incorporated by reference).

Immunosuppressive agent: A molecule, such as a chemical compound, small molecule, steroid, nucleic acid molecule, or other biological agent, that can decrease an immune response such as an inflammatory reaction.

Immunosuppressive agents include, but are not limited to an agent of use in treating arthritis (anti-arthritis agent). Specific, non-limiting examples of immunosuppressive agents are non-steroidal anti-inflammatory agents, cyclosporine A, FK506, and anti-CD4. In additional examples, the agent is a biological response modifier, such as Kineret® (anakinra), Enbrel® (etanercept), or Remicade® (infliximab), a disease-modifying antirheumatic drug (DMARD), such as Arava® (leflunomide), a nonsteroidal anti-inflammatory drug (NSAIDs), specifically a Cyclo-Oxygenase-2 (COX-2) inhibitor, such as Celebrex® (celecoxib) and Vioxx® (rofecoxib), or another product, such as Hyalgan® (hyaluronan) and Synvisc® (hylan G-F20).

Immune-Mediated disorder: A disorder that involves an unwanted immune response. Although immune recognition of "non-self" proteins is essential to avoid and eliminate infection, the immune response can sometimes be unwanted. Autoimmune diseases, such as rheumatoid arthritis, multiple sclerosis or insulin dependent diabetes mellitus, are the result of a pathological immune response against self antigens, and T cells are the primary mediators of autoimmunity. For example, rheumatoid arthritis is an autoimmune disorder, as are Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave.s disease, among others.

Rejection of transplanted organs and tissues are a further example of an immune-mediated disorder, and can often result in damage to and/or rejection of the transplant. Tissue rejection, also called graft-versus-host disease, is a consequence of organ or tissue transplantation caused by the transplant recipient's (host's) immune response to the transplanted organ/tissue which can damage or destroy it. Ordinarily, the immune response protects the body from potentially harmful substances (antigens) such as microorganisms, toxins, and cancer cells. The immune system distinguishes "self" from "foreign" by reacting to proteins on the surfaces of cells. It reacts against substances it recognizes as foreign (antigens). The presence of foreign blood or tissue in the body triggers an immune response that can result in blood transfusion reactions and transplant rejection when antibodies are formed against foreign antigens on the transplanted or transfused material. Before transplant, tissue is "typed" according to the antigens it contains (Histocompatibility antigens).

No two people (except identical twins) have identical tissue antigens. Therefore, in the absence of immunosuppressive drugs, organ and tissue transplantation would almost always causes an immune response against the foreign tissue (rejection), which would result in destruction of the transplant. Though tissue typing ensures that the organ or tissue is as similar as possible to the tissues of the recipient, unless the donor is an identical twin, no match is perfect and the possibility of organ/tissue rejection remains. Immunosuppressive therapy is used to prevent organ rejection.

Allergy is another example of an immune-mediated disorder. An allergy is a collection of symptoms caused by an exaggerated immune response or reaction to substances that do not trigger an immune response in most people. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions which could be provoked by many antigens. In practice these types do not necessarily occur in isolation from each other.

Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms.

Immune response: A response of a cell of the immune system, such as a B cell, T cell to a stimulus. In one embodiment, the response is specific for a particular antigen (an "antigen-specific response").

Inflammation: When damage to tissue occurs, the body's response to the damage is usually inflammation. The damage may be due to trauma, lack of blood supply, hemorrhage, autoimmune attack, transplanted exogenous tissue or infection. This generalized response by the body includes the release of many components of the immune system (e.g., IL-1 and TNF), attraction of cells to the site of the damage, swelling of tissue due to the release of fluid and other processes.

Inflammatory arthropathy: An inflammatory arthropathy is an inflammatory disease affecting one or more joints, for example an inflammatory disease that affects the synovial membranes of one or more joints. Inflammatory arthropathies include, for example, arthritis, ankylosing spondylitis, Reiter's syndrome, psoriatic arthropathy, enteropathis spondylitis, juvenile arthropathy, and reactive arthropathy.

Infectious agent: An agent that can infect a subject, including, but not limited to, viruses, bacteria, and fungi.

Examples of infectious virus include: Retroviridae (for example, human immunodeficiency viruses, such as HIV-1 (also referred to as HTLV-III, LAV or HTLV-III/LAV, or HIV-III; and other isolates, such as HIV-LP; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli.*

Examples of infectious fungi include, but are not limited to, *Cryptococcus neoformans, Histoplasma capsulatum, Coccidioides immitis, Blastomyces dermatitidis, Chlamydia trachomatis, Candida albicans.*

Other infectious organisms (such as protists) include: *Plasmodium falciparum* and *Toxoplasma gondii.*

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as dendritic cell, changes in form or function to become a functional mature cell, such as an APC.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e., molecules comprising a sugar (e.g., ribose or deoxyribose) linked to a phosphate group and to an exchangeable organic base, which is either a substituted pyrimidine (Py) (e.g., cytosine (C), thymine (T) or uracil (U)) or a substituted purine (Pu) (e.g., adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e., an oligonucleotide minus the phosphate) and any other organic base polymer. Oligonucleotides can be obtained from existing nucleic acid sources (e.g., genomic or cDNA), but are preferably synthetic (e.g., produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence and stimulates (e.g., has a mitogenic effect) vertebrate immune cells. The cytosine, guanine is unmethylated.

An "oligonucleotide delivery complex" is an oligonucleotide associated with (e.g., ionically or covalently bound to; or encapsulated within) a targeting means (e.g., a molecule that results in a higher affinity binding to a target cell (e.g., B-cell or natural killer (NK) cell) surface and/or increased cellular uptake by target cells). Examples of oligonucleotide delivery complexes include oligonucleotides associated with: a sterol (e.g., cholesterol), a lipid (e.g., cationic lipid, virosome or liposome), or a target cell specific binding agent (e.g., a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intra-articularly, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoimmune disorder. An example of a person with a known predisposition is someone with a history of diabetes in the family, or who has been exposed to factors that predispose the subject to a condition, such as lupus or arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Suppressive ODN: DNA molecules of at least eight nucleotides in length, wherein the oligodeoxynucleotide forms a G-tetrad, and has a CD value of greater than about 2.9. In a suppressive ODN the number of guanosines is at least two. In one embodiment, a suppressive ODN inhibits immune activation caused by CpG DNA when administered prior to, concurrently with, or after the administration of an CpG ODN. at least about 8 nucleotides in length.

Therapeutic agent: Used in a generic sense, it includes treating agents, prophylactic agents, and replacement agents.

Therapeutically effective amount of [a compound]: A quantity of a specified compound sufficient to achieve a desired effect in a subject being treated. For instance, this can be the amount of a suppressive ODN necessary to suppress CpG-induced immune cell activation in a subject, or a dose sufficient to prevent advancement, or to cause regression of a disease, or which is capable of relieving symptoms caused by a disease, such as pain or swelling.

An effective amount of a suppressive ODN can be administered systemically or locally. In addition, an effective amount of a suppressive ODN can be administered in a single dose, or in several doses, for example daily, during a course of treatment. However, the effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some embodiments, or from about 0.01 mg/kg to about 60 mg/kg of body weight, based on efficacy.

The suppressive ODNs disclosed herein have equal applications in medical and veterinary settings. Therefore, the general terms "subject" and "subject being treated" are understood to include all animals, including humans or other simians, dogs, cats, horses, and cows.

Therapeutically effective dose: A dose sufficient to prevent advancement, or to cause regression of the disease, or which is capable of relieving symptoms caused by the disease, such as pain or swelling.

III. Description of Several Embodiments

A. Suppressive Oligodeoxynucleotides and Guanosine-quadruplexes (G-tetrads)

The present disclosure relates to a class of DNA motifs that selectively inhibits or suppresses immune activation. Optimal activity is observed using multimers of these motifs, which are rich in G bases and capable of forming G-quadruplexes (G-tetrads). G-tetrads are G-rich DNA segments that can accommodate complex secondary and/or tertiary structures (see FIG. 1). The suppressive ODNs of the disclosure are highly specific (i.e., are neither toxic nor non-specifically immunosuppressive), and are useful for inhibiting an immune response. In one embodiment, a suppressive ODN is of use for blocking immunostimulation caused by CpG motifs in vivo and in vitro.

A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values. Oligonucleotides that form G-tetrads can also form higher-level aggregates that are more easily recognized and taken up by immune cells, for example, through scavenger receptors or by nucleolin.

The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. For instance, G-tetrad-forming ODNs can have CD values of 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of 8.5 is typically more suppressive than an ODN with a CD value of 2.9.

In some embodiments, the ODN is from about 8 to about 120 nucleotides in length. In particular examples, the ODN is from about 10 to about 30 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences.

In one embodiment, the suppressive ODNs have a sequence comprising at least one of the human telomere-derived TTAGGG suppressive motifs (see Example 1). In some examples, the ODN has at least one TTAGGG motif, and in certain examples, the ODN has multiple TTAGGG motifs. For example, in particular examples, the ODN has from about two to about 20 TTAGGG motifs, or from about two to about four TTAGGG motifs. In this embodiment, suppressive ODNs containing multiple TTAGGG repeats are the most suppressive. Single TTAGGG motifs are suppressive only when incorporated into larger ODNs with greater than 10 bases. The TTAGGG motifs may be in either the cis or trans position, i.e., they may be present on the same or on a different strand of DNA than that expressing the stimulatory CpG sequence.

Suppression of CpG-induced immune activation requires a G-tetrad-forming sequence that imposes the two-dimensional structure necessary for G-tetrad formation. Examples of suppressive ODN include, but are not limited to, those shown in FIG. 9. However, any oligonucleotide capable of forming G-tetrads may be used to suppress CpG DNA-induced immune activation. In particular examples, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Furthermore, in particular embodiments the ODN is modified to prevent degradation. In one embodiment, suppressive ODNs can include modified nucleotides to confer resistance to degradation. Without being bound by theory, modified nucleotides can be included to increase the stability of a suppressive ODN. Thus, because phosphorothioate-modified nucleotides confer resistance to exonuclease digestion, the suppressive ODNs are "stabilized" by incorporating phosphorothioate-modified nucleotides.

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (e.g., via an exo- or endo-nuclease). In one specific, non-limiting example, a modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODN of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogues, and any combination thereof. Those skilled in the art will recognize that any other standard technique may be used to synthesize the suppressive ODN described herein.

In one embodiment, a suppressive ODN is included in a delivery complex. The delivery complex can include the suppressive ODN and a targeting means. Any suitable targeting means can be used. For example, in some embodiments, a suppressive ODN is associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of oligodeoxynucleotide delivery complexes include a suppressive ODN associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Pharmaceutical Compositions

The suppressive ODNs described herein may be formulated in a variety of ways depending on the location and type of disease to be treated. Pharmaceutical compositions are thus provided for both local (e.g. topical or intra-articular) use as well as for systemic use. Therefore, the disclosure includes within its scope pharmaceutical compositions comprising at least one suppressive ODN formulated for use in human or veterinary medicine.

Pharmaceutical compositions that include at least one suppressive ODN as described herein as an active ingredient, or that include both a suppressive ODN and an additional anti-inflammatory or anti-arthritis factor as active ingredients, may be formulated with an appropriate solid or liquid carrier, depending upon the particular mode of administration chosen. Additional active ingredients include, for example, non-steroidal anti-inflammatory agents, such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, and rofecoxib, steroids, such as cortisone, dexamethasone, hydrocortisone, methylprednisolone, prednisolone, prednisone, and triamcinolone, and immunosuppressives, for example cyclosporin, tacrolimus, mycophenolic acid, and sirolimus.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

C. Therapeutic Uses

A method is disclosed herein for treating or preventing an immune mediated disorder in a subject. In one specific, non-limiting example, the immune mediated disorder is an autoimmune disease. In another specific, non-limiting example, the immune mediated disorder is an allergic reaction. In a further specific, non-limiting example, the immune mediated disorder is transplant rejection.

Autoimmune diseases include, but are not limited to inflammatory arthritis, Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave.s disease, among others.

Rejection of transplanted organs and tissues are a further example of an undesired consequence of normal immunity, which can often result in damage to and/or rejection of the transplant. Tissue rejection, also called graft-versus-host disease, is a consequence of organ or tissue transplantation caused by the transplant recipient's (host's) immune response to the transplanted organ/tissue which can damage or destroy it. Ordinarily, the immune response protects the body from potentially harmful substances (antigens) such as microorganisms, toxins, and cancer cells. The immune system distinguishes "self" from "foreign" by reacting to proteins on the surfaces of cells. It reacts against substances it recognizes as foreign (antigens). The presence of foreign blood or tissue in the body triggers an immune response that can result in blood transfusion reactions and transplant rejection when antibodies are formed against foreign antigens on the transplanted or transfused material. Before transplant, tissue is "typed" according to the antigens it contains (Histocompatibility antigens).

No two people (except identical twins) have identical tissue antigens. Therefore, in the absence of immunosuppressive drugs, organ and tissue transplantation would almost always causes an immune response against the foreign tissue (rejection), which would result in destruction of the transplant. Though tissue typing ensures that the organ or tissue is as similar as possible to the tissues of the recipient, unless the donor is an identical twin, no match is perfect and the possibility of organ/tissue rejection remains. Immunosuppressive therapy is used to prevent organ rejection.

Allergy is another example of an immune-mediated disorder. An allergy is a collection of symptoms caused by an exaggerated immune response or reaction to substances that do not trigger an immune response in most people. The term "allergy" has become synonymous with Type I hypersensitivity (IgE-mediated allergy). Four different types of hypersensitivity were described by Coomb and Gell (Types I, II, III and IV), as a pedagogical way to increase the understanding of different immune reactions which could be provoked by many antigens. In practice these types do not necessarily occur in isolation from each other.

Allergic diseases generally begin in childhood, although they can arise at any age. Development of allergic disease is associated with an allergic constitution due to heredity and to environmental and health factors. An allergic response involves an increased production of allergen-specific IgE antibodies, which may lead to clinical symptoms such as rhinitis, asthma, eczema, colic pains or diarrhea. A state of hyperreactivity often accompanies an allergic reaction. If this hyperreactivity occurs in the respiratory tract, everyday stimuli like dust, tobacco smoke, cold air and perfumes may lead to allergy-like symptoms.

The method includes administering a therapeutically effective amount of the suppressive ODN to a subject having or at risk of developing an immune-mediated disorder, thereby treating or preventing the immune-mediated disorder. In one embodiment, the suppressive ODN can be administered locally, such as by intra-articular injection. In another embodiment, the suppressive ODN is administered systemically. In one embodiment, the immune-mediated disorder is an autoimmune disease, an allergy, or graft-versus-host disease. In particular embodiments, the immune-mediated disorder is an inflammatory arthropathy.

In order to treat or prevent an immune-mediated disorder, a therapeutically effective amount of a suppressive ODN (see above) is administered to the subject. In one embodiment, the ODN has a CD value of greater than about 2.9, 3.0, 3.2, 3.4, 3.6, 3.8, 4.0, or 5.0. In some embodiments of the method, the ODN is from about 8 to about 120 nucleotides in length. In particular examples of the method, the ODN is from about 10 to about 30 nucleotides in length. Optionally, the suppressive ODN has multiple guanosine-rich sequences, for example, in certain embodiments of the method, the ODN has from about two to about 20 guanosine-rich sequences, or, more particularly, from about two to about four guanosine-rich sequences.

In some examples of the method, the ODN has at least one TTAGGG motif, and in certain examples, the ODN has multiple TTAGGG motifs. For example, in particular examples of the method, the ODN has from about two to about 20 TTAGGG motifs, or from about two to about four TTAGGG motifs. In particular examples of the method, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Combinations of these suppressive ODN are also of use. Thus, in one embodiment, more than one suppressive ODN, each with a different nucleic acids sequence, are administered to the subject. In several specific, non-limiting examples, at least two, at least three, or at least four suppressive ODN are administered to the subject.

In another embodiment, an additional anti-inflammatory agent or immunosuppressive agent is administered in conjunction with a suppressive ODN. The administration of the anti-inflammatory agent or immunosuppressive agent and the suppressive ODN can be sequential or simultaneous.

In particular examples, the immunosuppressive agent is a non-steroidal anti-inflammatory agent, such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, or rofecoxib, a steroid, such as cortisone, dexamethasone, hydrocortisone, methylprednisolone, prednisolone, prednisone, or triamcinolone, or an immunosuppressive agent, for example cyclosporin, tacrolimus, mycophenolic acid, or sirolimus.

In another embodiment an additional anti-inflammatory agent is administered in conjunction with a suppressive ODN. The agent can be an immunosuppressive, or an anti-arthritis agent. The administration of the anti-inflammatory agent and the suppressive ODN can be sequential or simultaneous.

In particular examples, the immunosuppressive agent is a biological response modifier, such as Kineret® (anakinra), Enbrel® (etanercept), or Remicade® (infliximab), a disease-modifying antirheumatic drug (DMARD), such as Arava® (leflunomide), a nonsteroidal anti-inflammatory drug (NSAIDs), specifically a Cyclo-Oxygenase-2 (COX-2) inhibitor, such as Celebrex® (celecoxib) and Vioxx® (rofecoxib), or another product, such as Hyalgan® (hyaluronan) and Synvisc® (hylan G-F20).

Thus, the suppressive ODNs disclosed herein may be administered to a subject for the treatment of immune-mediated disorders in that individual. ODN administration can be systemic or local. Local administration of the ODN is performed by methods well known to those skilled in the art. By way of example, one method of administration to the knee, hip and/or shoulder of an individual is by intra-articular injection. For administration to the knee, for example, the joint to be injected is washed with a betadine solution or other antiseptic. A solution of about one percent lidocaine hydrochloride is injected into the skin and subcutaneous tissue. A 3-way stopcock/needle assembly is utilized to administer the compound via an 18-30 gauge needle. The ODN is injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient is then confined to bed for approximately 24 hours to minimize movement and minimize leakage of ODN from the joint.

In other embodiment, the administration of the suppressive ODN is systemic. Oral, intravenous, intra-arterial, subcutaneous, intra-peritoneal, intra-muscular, and even rectal administration is contemplated.

In other embodiments, the method is a method of treating or preventing an autoimmune disease in a subject that involves contacting immune cells with a suppressive ODN, and transferring the immune cells to a subject having or at risk of developing an autoimmune disease, thereby treating or preventing the autoimmune disease. Without being bound by theory, these immune cells act to suppress immune activation in a subject. One specific, non-limiting example is dendritic cells. Thus, in certain examples, the immune cells, such as dendritic cells, are contacted with a suppressive ODN, and subsequently administered to a subject. The immune cells can be delivered alone, in conjunction with a suppressive ODN, and/or in conjunction with an additional immunosuppressive agent. The immune cells can be delivered either systemically or locally. In several specific, non-limiting examples, the cells are delivered parenterally, intravenously, intra-muscularly, sub-cutaneously, or intra-articularly.

Precise, effective quantities of cells can be readily determined by those who are skilled in the art and will depend, of course, upon the exact condition being treated by the particular therapy being employed. The cells can be transplanted to a desired location, or can be administered intravenously. Other agents, such as growth factors or immunosuppressive agents, can be administered in conjunction with the immune cells.

In other embodiments, suppressive ODNs are used to inhibit angiogenesis. In one embodiment, suppressive ODNs are utilized to inhibit angiogenesis in vivo. Thus, a suppressive ODN and a pharmacologically acceptable carrier are administered to a subject, such that angiogenesis is inhibited in the subject. Suitable subjects include, but are not limited to, subjects with a tumor, subjects with macular degeneration, or subjects with diabetic retinopathy. Suitable tumors include, but are not limited to bone, brain, breast, gastrointestinal, endocrine, eye, genitourinary, germ cell, gynecologic, head, neck, hematologic, leukemic, lung, lymphm, musculoskeletal, neurologic, respiratory, thoracic, and skin tumors.

In another embodiment, the CpG ODN is administered with a second anti-angiogenic factor. Specific, non-limiting examples of anti-angiogenic factors of use include, but are not limited to Macugen, rhuFab, alpha-interferon, thalidomide and prinomastat. The second anti-angiogenic agent can be administered simultaneously or sequentially with the suppressive ODN.

D. Kits

Further embodiments of the disclosure include kits useful for administering the suppressive ODN described herein in vivo or in vitro. For example, a kit useful for treating a subject with an autoimmune disease would comprise an appropriate dosage of suppressive ODN, as well as, optionally, any agents useful for enhancing the inhibitory effect of suppressive ODN. Other embodiments further include instructions for using the kit, and/or pre-filled syringes for administering the ODN to a subject.

Thus, in one embodiment, a kit is provided including a container of suppressive ODN (a sufficient amount for either a single use or multiple uses), and instructions the suppressive ODN. The instructions can be in written form, or can be provided in an electronic format, such as on a diskette or a CD-ROM. Instructions can also be provided in the form of a video cassette.

The subject matter of the present disclosure is further illustrated by the following non-limiting Examples.

EXAMPLES

Example 1

Repetitive Elements Present in Mammalian Telomeres Suppress Bacterial DNA-Induced Immune Activation This example demonstrates the ability of TTAGGG multimers to inhibit CpG-induced immune activation.

A. General Methods

Reagents

Endotoxin-free phosphorothioate or phosphodiester ODNs were synthesized at the CBER core facility. 7-DG modified ODNs were synthesized using the 10-camphorsulphonyl-oxaziridine oxidization protocol recommended by the manufacturer (Glen Research, Sterling, Va.). Mammalian DNA was isolated from calf thymus and murine spleen (Wizard Genomic DNA purification kit, Promega, Madison, Wis.). *E. coli* was obtained from Sigma (St. Louis, Mo.). Telomerase knockout mice were provided by Dr. Carol Greider (Johns Hopkins Univ., Baltimore, Md.). All DNA obtained from commercial providers was re-purified to eliminate endotoxin (<0.1 U/mg). Double stranded DNA was converted to single stranded DNA by heat denaturing at 95° C. for 5' followed by cooling on ice. BAL-31 (New England Biolabs, Beverly, Mass.) digestion of CT DNA was continued for 2 h at 30° C. according to manufacturer's recommendations. At the end of the incubation, the enzyme was inactivated at 65° C. for 10 min. Plasmid encoding for 1.6 kb long TTAGGG repeat was a generous gift from Dr. Jerry Shay (University of Texas Southwestern Medical Center, Dallas, Tex.). Non-telomere coding plasmid was from Vical (San Diego, Calif.).

Mice

Specific pathogen-free male BALB/c mice (Jackson Laboratories, Bar Harbor, Me.) were housed in sterile micro-isolator cages in a barrier environment and injected i.p. with 400 g of CpG ODN plus 200 g of suppressive or control ODN. Spleen cells were harvested 6 h later and monitored for cytokine production after 36 h. In order to measure the pEPO transgene expression levels, female Balb/c mice (4-6 weeks old) were injected with 30 μg of pVRmEPO (a kind gift of Vical, San Diego, Calif.) plasmid in sterile saline into the anterior tibialis muscle alone or in combination with 50 μg of control or suppressive ODN. Hematocrits were measured as described (Tripathy et al., *Proc Natl Acad Sci USA*. 93:10876-80, 1996) on blood collected by tail vein puncture.

Cytokine and IgM ELISA Assays

Immulon 2 microtiter plates (Dynex Technologies Inc., Chantilly Va.) were coated with anti-cytokine or anti-IgM antibodies (Pharmingen, San Diego Calif.) and then blocked with PBS-1% BSA. Serially diluted culture supernatant or serum was added for 2 h. Cytokine was detected using biotinylated anti-cytokine Ab followed by phosphatase-streptavidin (Pharmingen) whereas bound IgM was detected using phosphatase-conjugated anti-IgM antibodies (Southern Biotechnology Associates, Birmingham, Ala.) as described.

Detection of Co-stimulatory Molecule Expression by FACS $2 \times 10^6$ spleen cells/ml were incubated with ODN for 24 h. Cells were washed, fixed with 5% paraformaldehyde for 15 min, and stained with PE-labeled anti CD-40, anti CD-86, and anti ICAM-1 (Pharmingen, San Diego, Calif.) for 30 min at RT. Cells were washed, re-suspended in PBS/BSA (supplemented with Azide), and analyzed by FACSort (Becton Dickinson, San Jose, Calif.).

Cytokine RT-PCR

Spleen cells were isolated 6 h after CpG ODN injection. Total RNA was extracted, reverse-transcribed, and amplified in a standard PCR reaction for 24 cycles using primers specific for murine IL-6, IL-12, and IFN as previously described (Takeshita et al., *Neuroreport* (2001)). PCR amplified material was separated on 1.5 agarose gels and visualized under UV light after ethidium bromide staining.

Cell Transfection and Luciferase Assay

HEK 293 ($5 \times 10^4$) cells (ATCC, Manassas, Va.) were transfected with 0.8 μg of vector plasmid (pCIneo, Promega, Madison, Wis.), pCIneo-mTLR9, plus 0.1 μg of p5xNF-kB-luc (Stratagene, Lajolla, Calif.) and 0.1 μg of pSV-beta-galactosidase (Promega) and incubated overnight at 37° C. The cells were then stimulated with indicated ODN for 24 h. Cells were then harvested and luciferase assay was performed as recommended by the manufacturer (Promega). Beta-galactosidase activity was used to normalize the data.

Measurement of Circular Dichroism

A Jasco J-720A spectropolarimeter was used to measure the circular dichroism of ODN (50 g/ml in 0.1×PBS). Data is expressed as the mean peak ellipticity (mdeg/abs) of 5-10 readings/sample in the 260-270 nm range.

Statistical Analysis

In vitro assays were performed in triplicate on at least 3 different spleen cell preparations. All in vivo experiments were performed on a minimum of 5-10 mice/group. Statistical significance was evaluated using Student's t test. Correlation analysis is computed by linear correlation analysis between CD data vs % suppression.

B. TTAGGG Multimers Inhibit CpG-induced Immune Activation

The ability of TTAGGG multimers to inhibit CpG-induced immune activation was tested. Initial experiments showed that ODNs containing suppressive motifs inhibit CpG-induced immune activation in a dose-dependent fashion (FIG. 2A).

ODNs containing the largest number of TTAGGG repeats (n=4) were the most suppressive (p<0.001; FIG. 2B). Single TTAGGG hexamers were suppressive only when incorporated into larger ODNs (>10 bases in length), and were somewhat less active than TTAGGG multimers. TTAGGG motifs were suppressive both in cis and in trans, i.e., they inhibited immune activation when present on the same or on a different strand of DNA than that expressing the stimulatory CpG sequence (FIGS. 2C and D). This inhibitory activity was exquisitely specific: even high concentrations of suppressive ODNs had no effect on mitogen-induced immune responses (FIG. 2D), indicating that suppressive ODN were neither toxic nor non-specifically immunosuppressive.

C. Suppression is Mediated by Poly-G Sequences

The bases contributing to this suppressive activity were identified by systematically modifying ODNs containing single TTAGGG motifs. Substitutions outside the telomere-derived sequence did not significantly affect suppression. Replacing multiple bases in the TTA region of the TTAGGG motif also had little effect on the suppressive activity (FIG. 2E). In contrast, replacing two or more of the Gs in this motif substantially reduced the ODN's ability to block CpG-induced immune activation (FIG. 2E). These results suggest that suppression is mediated by the poly-G sequence itself, or the two-dimensional structure imposed by that sequence.

D. Suppression is Mediated by the Two-dimensional Structure of the Motifs

To differentiate between these alternatives, individual Gs were replaced by 7-deaza guanosine (7-DG) analogues. These 7-DG substitutions did not alter the base sequence of the ODN but did prevent Hoogsteen hydrogen bonding between guanosines, thereby reducing G tetrad formation (Hurley et al., *Trends Pharmacol. Sci.* 21:136-142, 2000; Lilley et al., *EMBO J.* 13:993-1001, 1994). The resultant loss in secondary structure is reflected by a loss in circular dichroism (Lilley et al., *EMBO J.* 13:993-1001, 1994). ODNs capable of forming G tetrads typically have peak CD values >2, while those without such secondary structure have circular dichroism values <1.4 (FIG. 2).

Figure 3A:
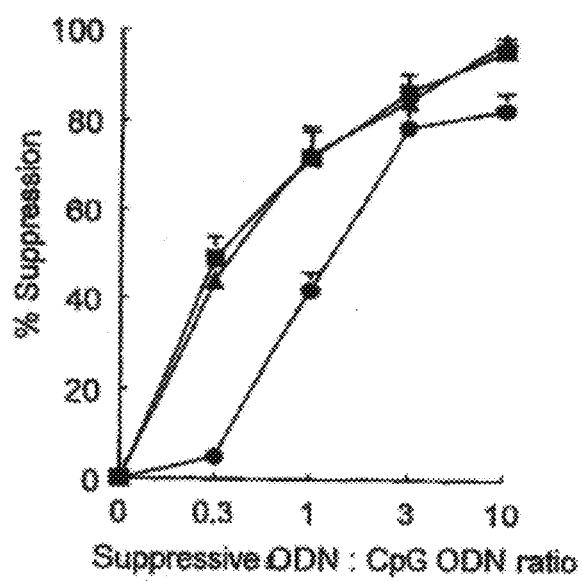
FIG. 3A is a graph showing that oligonucleotides (ODNs) containing suppressive motifs inhibit CpG-induced immune activation in a dose dependent fashion.
Figure 3B:
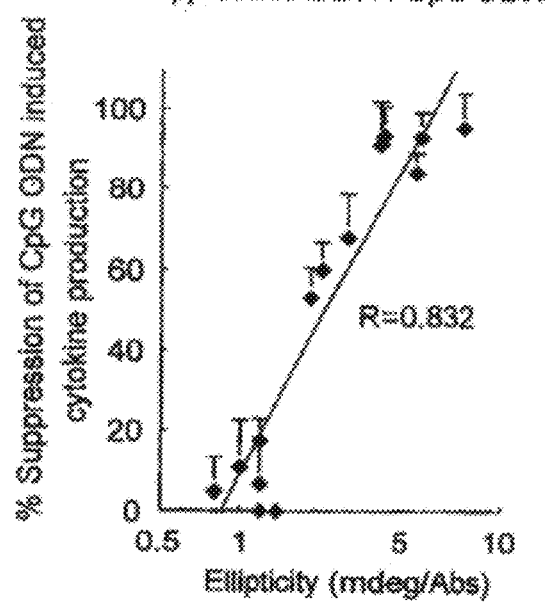
FIG. 3B is a graph showing G-tetrad formation and suppressive activity of phosphorothioate and 7-DG modified ODNs.

Introducing a 7-DG substitution significantly reduced an ODN's ability to form a G-tetrad and to mediate suppression (p<0.001, FIG. 3). To confirm that G-tetrad formation was critical to suppression, ODNs were synthesized that lacked the TTAGGG motif but still formed G-tetrads. These novel ODNs suppressed CpG ODN and bacterial DNA induced immune stimulation by >90% (p<0.001; FIG. 2F). Indeed, there was a consistent correlation between G-tetrad forming ability and suppressive activity (R=0.832, FIG. 3B).

E. Mechanism of Suppressive ODN Activity

The mechanism by which suppressive ODNs inhibit immune activation was explored. We confirmed that both bacterial DNA and CpG ODN stimulate DNA-dependent protein kinase activity in vitro. Of particular interest, this activity was specifically blocked by TTAGGG multimers and other G tetrad forming ODN, but not their 7-DG modified analogues. These findings indicate that suppressive motifs inhibit CpG-dependent DNA-PK$_{os}$ activation of immune cells. In contrast, suppressive ODNs did not block the binding or internalization of CpG ODNs mediated by Toll-like receptor 9.

Example 2

Effect of Suppressive ODNs on CpG-induced Immune Action

This example demonstrates the kinetics, magnitude, and nature of the immune inhibition elicited by suppressive motifs. Previous studies established that the immunostimulatory activity of CpG DNA can be reversed several hours later either by removing the stimulatory DNA or adding suppressive DNA. The same cells that interact with stimulatory motifs also recognize suppressive motifs. When both sequence types are present on the same strand of DNA, recognition proceeds in a 5'->3' direction. Suppression is generally dominant over stimulation, although a motif in the 5' position can interfere with recognition of a motif immediately downstream. Understanding the rules governing cellular responses to stimulatory and suppressive motifs facilitates the design of ODN for therapeutic uses.

A. General Methods

Animals:

Female Balb/c mice were obtained from the Jackson Laboratories (Bar Harbor, Me.). The mice were housed under specific pathogen free conditions, and used at 8-20 weeks of age. All studies involved protocols approved by the CBER Animal Care and Use Committee.

Oligodeoxynucleotides:

Studies utilized phosphorothioate modified ODNs that were synthesized at the CBER core facility Verthelyi, D., et al., *J Immunol* (2001) 166:2372. The following ODNs were used: immunostimulatory ODN1466 (TCAACGTTGA; SEQ. ID NO: 26) and ODN1555 (GCTAGACGTTAGCGT; SEQ. ID NO: 27), control ODN1471 (TCAAGCTTGA; SEQ. ID NO: 28) and ODN1612 (GCTAGAGCTTAGGCT; SEQ. ID NO: 29), suppressive ODN1502 ( GAGCAAGCTGGACCTTCCAT; SEQ. ID NO: 20) and ODNH154 (CCTCAAGCTTGAGGGG; SEQ. ID NO: 1). Underlined bases represent the 10-mer sequences that were incorporated into complex multi-determinant ODN used in some experiments. There was no detectable protein or endotoxin contamination of these ODN.

Mammalian DNA was purified from BALB/c spleens (Wizard Genomic DNA purification kit, Promega, Madison, Wis.). *E. coli* DNA was obtained from Gibco BRL (Rockville, Md., USA). Endotoxin contamination in these preparations was <0.1 U/ml after purification Klinman, D. M., et al., *J. Immunol.* (1997) 158:3635. Double stranded DNA (dsDNA) was converted to single stranded DNA (ssDNA) by heat denaturing at 95° C. for 5' followed by immediate cooling on ice.

Cytokine ELISA Assays:

Single spleen cell suspensions were washed 3 times and re-suspended in RPMI-1640 supplemented with 5% heat inactivated fetal calf serum (FCS), 1.5 mM L-glutamine and 100 U/ml of penicillin/streptomycin. $5 \times 10^5$ cells/well were cultured in flat-bottomed microtiter plates (Costar, Corning, N.Y.) with 1 uM ODN for 18-24 h. Culture supernatants were collected, and cytokine levels measured by ELISA. In brief, 96 well Immulon H2B plates were coated with cytokine-specific antibodies and blocked with PBS1% BSA as previously described in Klinman, D. M., and Nutman, T. B., *Current Protocols in Immunology* (1994), J. E. Coligan, A. M. Kruisbeek, D. H. Margulies, E. M. Shevach, and W. Strober, eds., Greene Publishing Associates, Brooklyn, N.Y. Culture supernatants were added, and bound cytokine detected by the addition of biotin labeled secondary antibodies followed by phosphatase-conjugated avidin and a phosphatase-specific colorimetric substrate (PNPP, Pierce, Rockford, Ill.). Standard curves were generated using recombinant cytokines. The detection limit for these assays was: 0.8 U/ml for IFNg, 0.1 ng/ml for IL-6 and 0.1 ng/ml for IL-12. All assays were performed in triplicate.

Cytokine-specific ELIspot Assays:

A single spleen cell suspension prepared in RPMI 1640 plus 5% FCS was serially diluted onto plates pre-coated with anti-cytokine Abs. Klinman, D. M., and Nutman, T. B., *Current Protocols in Immunology* (1994), J. E. Coligan, A. M. Kruisbeek, D. H. Margulies, E. M. Shevach, and W. Strober, eds., Greene Publishing Associates, Brooklyn, N.Y. Cells were incubated with 1 uM ODN at 37° C. for 8-12 h, and their secretion of cytokine detected colorimetrically as previously described. Klinman, D. M., and Nutman, T. B., *Current Protocols in Immunology* (1994), J. E. Coligan, A. M. Kruisbeek, D. H. Margulies, E. M. Shevach, and W. Strober, eds., Greene Publishing Associates, Brooklyn, N.Y.

Cell-surface Binding and Internalization of ODN:

Spleen cells ($2\times10^6$/ml) were incubated with 1 uM of unlabeled and/or fluorescent-labeled ODN for 10' at 4° C. (binding experiments) or at 37° C. for 1 h (uptake experiments Gursel, M., et al., *J. Leuko. Biol.* (2001) in press. Cells were washed, fixed, and analyzed by FACScan (Becton Dickinson, San Jose, Calif.).

Statistical Analysis:

Statistically significant differences between two groups were determined using the Wilcoxon Rank Sum Test. When comparing more than two groups, differences were determined using a 2-tailed non-parametric ANOVA with Dunn's post-test analysis. p values <0.05 were considered significant.

B. Mammalian DNA Suppresses CpG DNA-Induced Immune Activation

Figure 4:
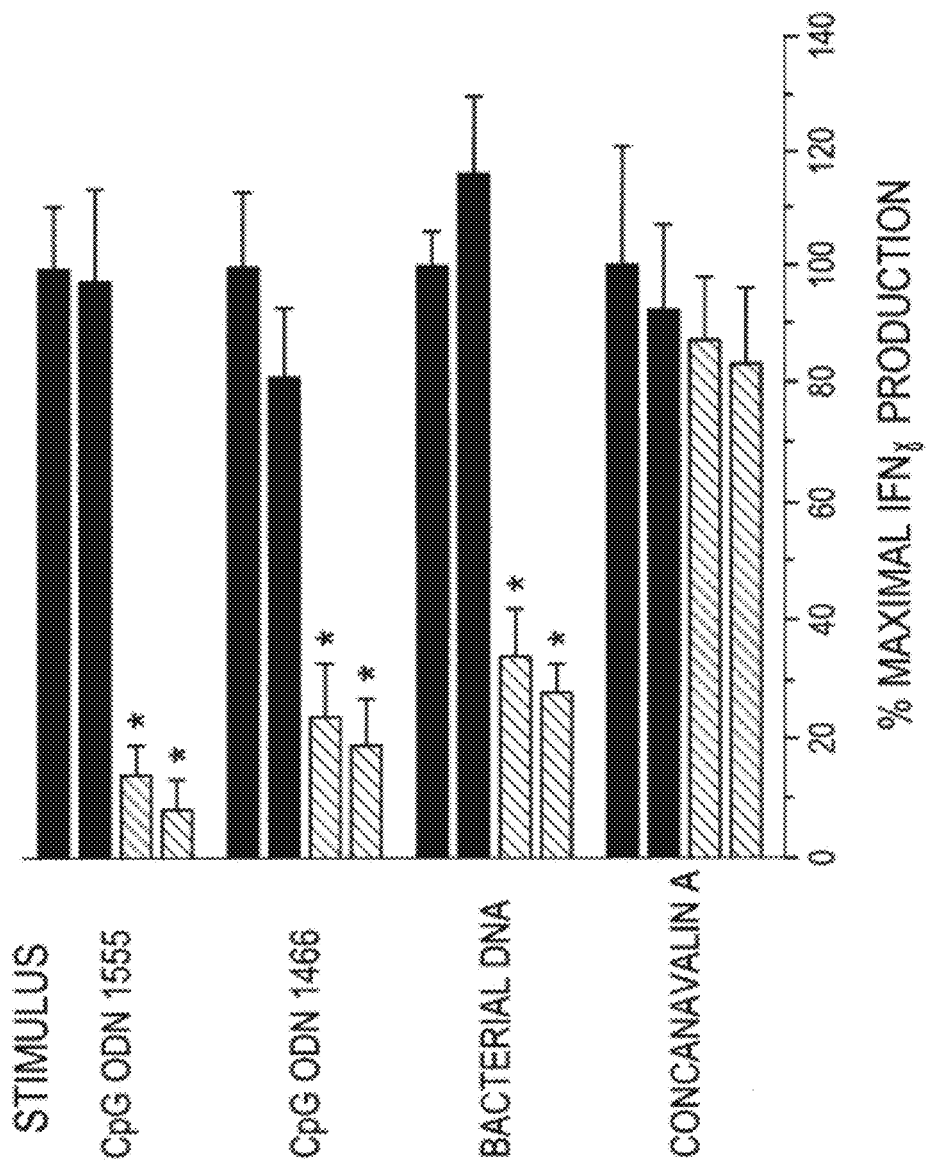
FIG. 4: is a graph showing the effect of suppressive ODN on CpG DNA and Con A induced IFNγ production. BALB/c spleen cells were stimulated with 1 μM CpG ODN (ODN1555, ODN1466), 50 μg/ml of bacterial DNA, or 5 μg/ml Con A. The response of these cultures was compared to cells co-stimulated with 1 μM of control ODN1612, suppressive ODN1502 or suppressive ODNH154. The number of IFNγ secreting cells was determined by ELIspot after 18 h. Data represent the average+SD of triplicate cultures. The experiment was repeated three times with similar results.

Single stranded bacterial DNA and synthetic ODN containing unmethylated CpG motifs stimulate immune cells to mature, proliferate and produce cytokines, chemokines, and Ig. Klinman, D. M., et al., *Proc. Natl. Acad. Sci. USA* (1996) 93:2879; Roman, M., et al., *Nature Medicine* (1997) 3:849. (Roman et al., (1997) *Nature Medicine* 3:849; Yamamoto et al., (1992) *J. Immunol.* 148:4072; Krieg et al., (1995) *Nature* 374:546). These effects can be blocked by "poly-G" and/or "GC" rich DNA motifs (Krieg et al., (1998) *Proc. Natl. Acad. Sci.* 95:12631; Pisetsky et al., (1995) *NY Acad. Sci.* 772:152). Scores of ODNs were synthesized and tested, and eventually several were identified that selectively inhibited CpG-induced immune responses. The two most active of these suppressive ODN (ODN1502 and ODNH154) were selected for detailed study. As seen in FIG. 4, suppressive ODN blocked a majority of the IFNγ production induced by bacterial DNA or CpG ODN (p<0.01). Suppressive ODN were neither toxic nor broadly immunosuppressive, as they did not interfere with the mitogenic activity of LPS or Con A (FIG. 4).

Figure 5:
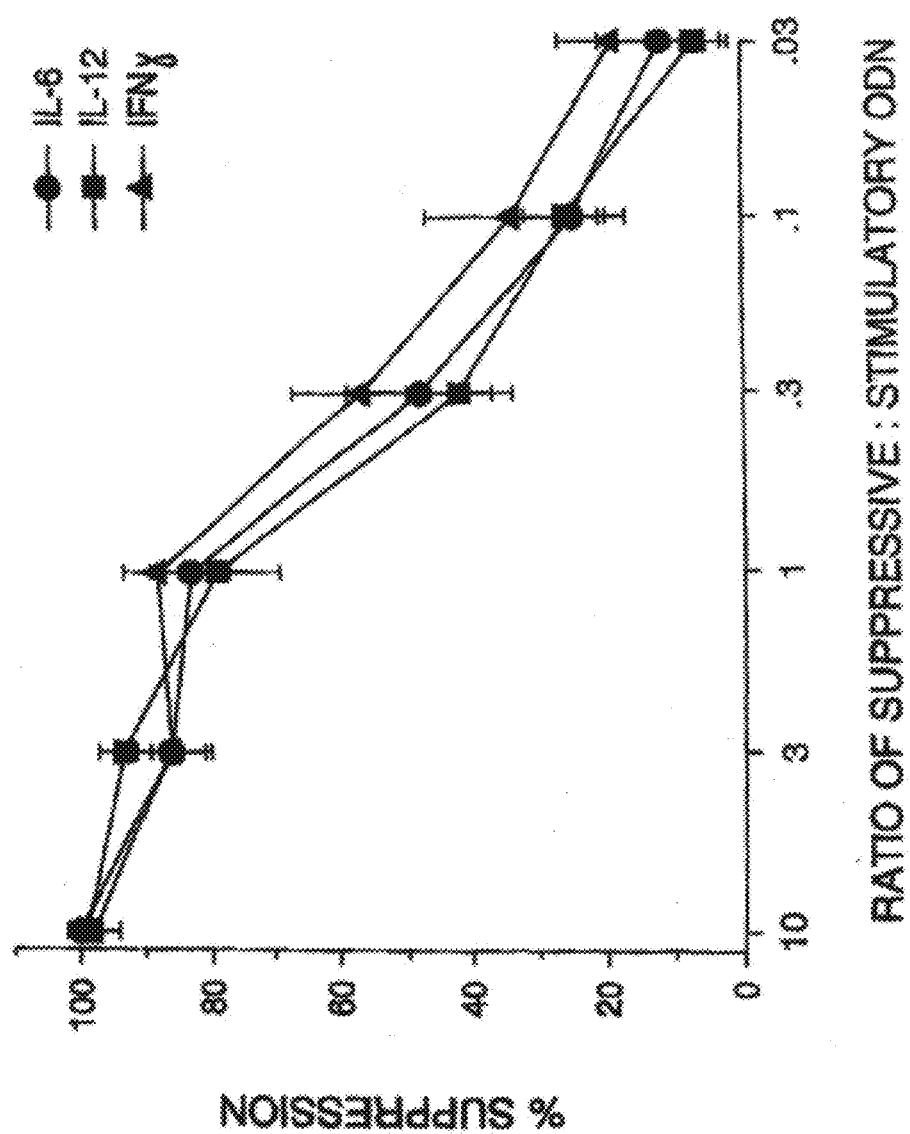
FIG. 5: is a graph showing the concentration effects of suppressive ODN. BALB/c spleen cells were stimulated with 1 μM CpG ODN1555 or ODN1466 plus increasing amounts of suppressive ODN1502 or ODNH154. Cytokine levels in culture supernatants were measured by ELISA after 24 h. Results represent the mean+SD of 4 different experiments.
Figure 6:
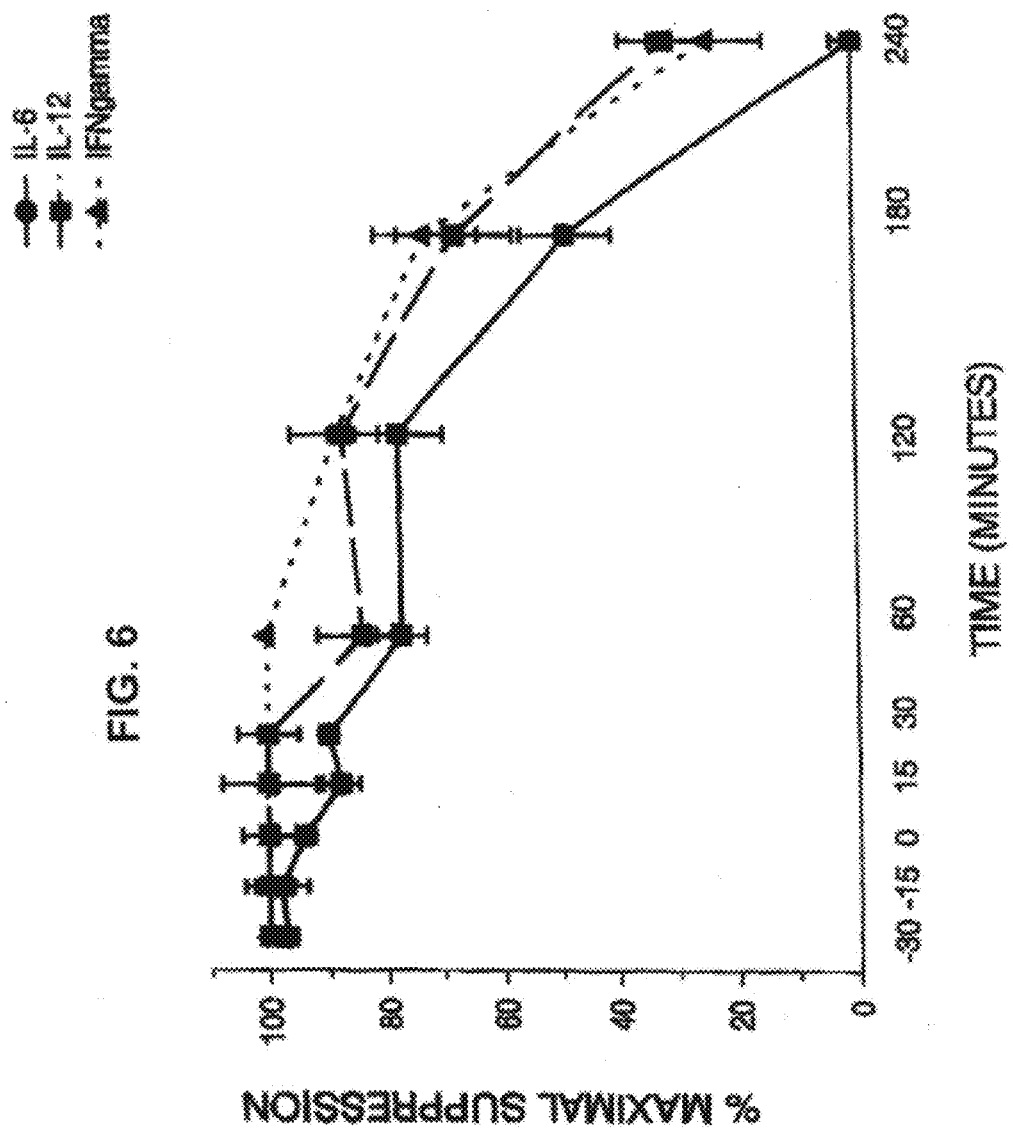
FIG. 6: is a graph showing the kinetics of suppressive ODN. BALB/c spleen cells were stimulated with 1 μM CpG ODN1555. At various times, 1 μM suppressive ODN1520 was added. Cytokine levels in culture supernatants were measured by ELISA after 24 h. Results represent the mean of two independent experiments.

The activity of suppressive ODNs was concentration dependent, with 50% suppression being achieved at a suppressive:CpG ODN ratio of approximately 1:3 (FIG. 5). To examine the kinetics of this inhibition, suppressive ODN were added to BALB/c spleen cells at various times after CpG-induced stimulation. Maximal inhibition was observed when suppressive ODN were co-administered with CpG ODN, although statistically significant inhibition persisted when suppressive ODN were added up to 3 h later (FIG. 6). These findings suggest that CpG induced immune activation is an ongoing process, and can be inhibited after the stimulatory signal is delivered.

To test this conclusion, spleen cells were incubated with CpG ODN for various periods and cytokine production analyzed after 24 h. Cells stimulated with CpG DNA for 8 h produced 90% as much cytokine as cells stimulated continuously for 24 h (FIG. 7). Cells treated with CpG ODN for only 4 h produced half as much cytokine, while cells treated with CpG DNA for <2 h showed only minimal activation (FIG. 7).

These findings support the conclusion that CpG-induced cellular activation is reversible for several hours.

C. Suppressive ODNs do not Block CpG ODN Uptake or Induce the Production of Inhibitory Factors The results described above indicate that CpG-induced immune activation can be reversed either by adding suppressive ODNs or by removing stimulatory ODNs. This suggests that suppressive ODNs block the ongoing uptake of CpG DNA. Yet FACS analysis demonstrated that neither cell surface binding nor internalization of FITC-labeled CpG ODN was significantly reduced by suppressive ODN at concentrations that blocked cytokine production by approximately 75% (FIG. 8).

The possibility that suppressive motifs might induce the production of a factor that blocks CpG-dependent immune activation was then investigated. Initial studies established that BALB/c spleen cells pre-incubated with suppressive ODN remained unresponsive to CpG-induced stimulation for several hours (Table I, line 3). If this non-responsive state was mediated by a soluble factor (or inhibitory cell-cell interactions) then cells pre-treated with suppressive ODN should block CpG-induced stimulation of naive spleen. As seen in Table I, cells treated with suppressive ODN had no significant effect on CpG dependent cytokine production by fresh splenocytes.

TABLE I

Effect of mixing cells treated with suppressive versus stimulatory ODN

| Cells pre-treated with suppressive ODN | Fresh cells | ODN added during culture | % maximal cytokine production | |
|---|---|---|---|---|
| | | | IL-6 | IL-12 |
| − | + | CpG | 100 ± 13 | 100 ± 6 |
| − | + | Control | 3 ± 2 | 7 ± 2 |
| + | − | CpG | 9 ± 6 | 6 ± 2 |
| + | − | Control | 0 ± 0 | 0 ± 0 |
| + | + | CpG | 86 ± 16 | 105 ± 12 |
| + | + | Control | 0 ± 0 | 0 ± 0 |

BALB/c spleen cells were treated with 1 uM suppressive $ODN_{1502}$ for 2 h and then washed (first column). These cells were added to naive splenocytes (second column) plus 1 uM of control $ODN_{1471}$ or CpG $ODN_{1555}$. IL-6 and IL-12 levels in culture supernatants were measured by ELISA after 18 h. Results represent the average + SD of triplicate assays, each standardized to the response induced by bacterial DNA (62 pg/ml IL-6; 134 pg/ml IL-12).

D. Cellular Recognition of Suppressive Versus Stimulatory Motifs

The above studies establish that suppressive motifs on one strand of DNA block the immune activation induced by stimulatory motifs on a different strand (i.e., trans suppression). To better understand the interaction between suppressive and stimulatory motifs, ODNs containing both were synthesized. In the simplest case, a 20-mer was constructed in which a CpG motif was placed immediately 5' to a suppressive motif (referred to as [CpG-Sup] ODN).

Experiments showed that this ODN was stimulatory, triggering murine spleen cells to produce IL-6, IL-12 and IFNγ to the same extent as an ODN of the same length in which the suppressive motif was replaced by a 'control' sequence (i.e., one that was neither stimulatory nor suppressive, Table II). [CpG-Sup] ODNs also failed to block the immune activation induced by an independent CpG ODN (Table II). These results suggest that a suppressive motif is inactive when located immediately 3' to a CpG motif on the same strand of DNA. Similar results were obtained in studies of additional [CpG-Sup] ODNs that utilized different stimulatory and suppressive motifs.

TABLE II

Effect of motif position on immunostimulatory activity

| Location of motifs | # of cytokine secreting cells | | |
|---|---|---|---|
| (5' → 3') | IL-6 | IL-12 | IFNg |
| CpG ODN* | 79 ± 13 | 1980 ± 230 | 260 ± 40 |
| [CpG-Sup] ODN* | 72 ± 14 | 2080 ± 480 | 230 ± 60 |
| [Sup-CpG] ODN | 0 ± 0 | 140 ± 30 | 0 ± 0 |
| [CpG-Cont] ODN* | 64 ± 12 | 2210 ± 130 | 284 ± 34 |
| [Cont-CpG] ODN* | 80 ± 11 | 1942 ± 88 | 238 ± 28 |
| [Cont-Sup] ODN | 8 ± 2 | 184 ± 34 | 36 ± 8 |
| [CpG-Sup] ODN + Sup ODN | 4 ± 2 | 226 ± 38 | 28 ± 6 |
| [Sup-CpG] ODN + CpG ODN* | 7 ± 3 | 250 ± 32 | 34 ± 9 |

$10^6$ BALB/c spleen cells were co-incubated with 1 uM of each ODN. Complex ODN (20 bp in length) were constructed from 10-mers containing suppressive (Sup), stimulatory (CpG) or control (Cont) motifs. The number of cytokine secreting cells/$10^6$ was determined by ELIspot after 24 h of stimulation. Equivalent results were derived using combinations of motifs derived from two different stimulatory ($ODN_{1555}$ and $ODN_{1466}$), control ($ODN_{1471}$ and $ODN_{1612}$) and suppressive ($ODN_{1502}$ and $ODN_{H154}$) ODN. Results represent the average ± SD of triplicate assays involving at least two ODN of each type.
*Stimulatory ODN,
$p < .05$.

To better understand this phenomenon, longer ODNs were synthesized in which the CpG and suppressive motifs were separated by progressively longer CT spacers. Adding a 5 base spacer generated an ODN that was still stimulatory (Table III). However, separating the motifs by >10 bases yielded ODNs that were suppressive, since they blocked the stimulatory activity of co-administered CpG ODNs (Table III).

TABLE III

Effect of distance between motifs on ODN activity

| | Cytokine producing cells (% maximum) | | |
|---|---|---|---|
| ODN | IL-6 | IL-12 | IFNg |
| CpG ODN* | 100 ± 11 | 100 ± 7 | 100 ± 10 |
| CpG ODN* + Cont ODN | 97 ± 14 | 98 ± 9 | 100 ± 17 |
| CpG ODN* + Sup ODN | 16 ± 6 | 21 ± 6 | 18 ± 5 |
| [CpG-Sup] ODN* | 87 ± 12 | >100 ± 14 | 92 ± 14 |
| [CpG-5 bases-Sup] ODN* | >100 ± 4 | >100 ± 21 | >100 ± 22 |
| [CpG-10 bases-Sup] ODN | 38 ± 6 | 64 ± 15 | 42 ± 7 |
| [CpG-20 bases-Sup] ODN | 7 ± 4 | 48 ± 13 | 24 ± 8 |
| [CpG-20 bases-Cont] ODN* | 94 ± 7 | >100 ± 14 | 99 ± 11 |
| [Sup-CpG] ODN | 0 ± 0 | 0 ± 0 | 0 ± 0 |
| [Sup-20 bases-CpG] ODN | 8 ± 5 | 9 ± 3 | 2 ± 1 |
| [CpG-Sup] ODN* + CpG ODN* | >100 ± 16 | >100 ± 15 | 98 ± 13 |
| [CpG-5 bases-Sup] ODN* + CpG ODN* | >100 ± 18 | >100 + 11 | 98 ± 20 |
| [CpG-10 bases-Sup] ODN + CpG ODN* | 58 ± 7 | 75 ± 9 | 66 ± 9 |
| [CpG-20 bases-Sup] ODN + CpG ODN* | 27 ± 5 | 26 ± 10 | 30 ± 8 |
| [Sup-CpG] ODN + CpG ODN* | 9 ± 4 | 11 ± 4 | 8 ± 5 |
| [Sup-20 CT-CpG] ODN + CpG ODN* | 5 ± 1 | 9 ± 3 | 13 ± 2 |

BALB/c spleen cells were stimulated in vitro with 1 uM of each ODN, and the number of cells activated to secrete cytokine determined 8 h later by ELIspot. The percent of cells activated to secrete cytokine was calculated by the formula: (# of cells activated by test ODN) − (background)/(# of cells activated by CpG ODN) − (background) × 100%.
Two different control ($ODN_{1471}$ and $ODN_{1612}$), CpG ($ODN_{1466}$ and $ODN_{1555}$) and suppressive ($ODN_{1502}$ and $ODN_{H154}$) ODN gave similar results in these experiments. Results represent the average of 2-4 assays/data point. Table II shows typical numbers of cytokine secreting cells/$10^6$.
*Stimulatory ODN,
$p < .05$.

The trivial possibility that the CT spacer somehow reduced CpG activity was eliminated by substituting a "control" motif for the 3' suppressive motif. The resulting ODNs were fully stimulatory (Table III).

The impact of placing a suppressive motif 5' to a CpG motif was then examined. ODNs with a suppressive motif in the 5' position induced little or no immune activation, even when the CpG motif was shifted up to 20 by downstream from the suppressive motif (Tables II and III). This lack of activity could not be attributed to the 3' location of the CpG motif, since CpG ODNs with a 'control' sequence at the 5' end were immunostimulatory. All ODNs containing a suppressive motif in the 5' position also inhibited co-administered CpG ODN (Tables II and III). These findings suggest that the relative position of stimulatory and suppressive motifs determines the immunomodulatory properties of DNA.

Example 3

Suppressive ODN Permit Higher Levels of Transgene Expression

This example demonstrates that suppressive ODNs permit higher levels of transgene to be expressed when the transgene vector contains immunostimulatory CpG motifs.

Balb/C mice were injected intramuscularly with 30 μg vector encoding erythropoietin alone or together with 50 μg of each suppressive ODN. Suppressive ODN was either co-injected at the time of vector injection or was given 3 days prior to vector injection. Transgene expression was studied by measuring the hematocrit levels from blood at various intervals. Data represent mean+S.D. for three animals. Suppressive ODN permitted higher levels of transgene expression (FIG. 9).

Without being bound by theory, it is believed that this increase in transgene expression is limited by immune activation triggered by immunostimulatory CpG motifs in the erythropoietin construct. Administration of suppressive ODN inhibits this immune activation and permits the transgene to be expressed at higher levels.

Example 4

Suppressive ODN Blocks the Activity of CpG Motifs In Vivo

This example shows that suppressive ODNs work in vivo to directly counteract the activity of immunostimulatory CpG motifs.

The effect of Suppressive ODN on CpG ODN-induced immune protection was studied. Balb/c mice were injected IP with 50 μg of each ODN. Five days later, animals were challenged IP with $10^3$ LD50 of *Listeria monocytogenes*. Survival was monitored for >3 weeks, although all animals that succumbed to infection died within one week of challenge. Suppressive ODN blocked the activity of CpG motifs in vivo (FIG. 10).

Example 5

Reduction of CpG-Induced Arthritis by Suppressive Oligodeoxynucleotides

This example demonstrates the influence of CpG DNA and suppressive ODNs on the propensity of the host to develop arthritis, and indicates that the mechanism of suppressive ODN action is mediated by Cd11c positive cells.

A. General Methods
Animals:

Female BALB/c mice were obtained from the Jackson Laboratories (Bar Harbor, Me.). ACUC approved studies were conducted using 8-20 week old mice.

Oligodeoxynucleotides:

ODNs were synthesized at the CBER Core Facility. Sequences of the phosphorothioate ODN used were:

```
                            (SEQ ID NO: 30)
CpG:            GCTAGACGTTAGCGT (SEQ ID NO: 1)
suppressive:    CCTCAAGCTTGAGGGG (SEQ ID NO: 31)
control:        GCTAGATGTTAGCGT.
```

All ODN were free of detectable protein or endotoxin contamination.

Experimental Protocol:

25 g of ODN in 6 μl of PBS was injected into the knee joint using a 30 gauge needle. In some studies, knees were re-injected with PBS or 25 μg of suppressive ODN 24-48 h after initial CpG ODN administration. Joint swelling was measured in the coronal plane using a micrometer caliper. Histologic analysis was performed by a blinded investigator on fixed, decalcified and paraffin embedded sections stained with hematoxylin/eosin.

TNFα Assays:

Single spleen cell suspensions were prepared in RPMI-1640 supplemented with 5% heat inactivated fetal calf serum, 1.5 mM L-glutamine and 100 U/ml of penicillin/streptomycin. $5 \times 10^5$ cells/well were cultured in flat-bottomed microtiter plates (Costar, Corning, N.Y.) with ODN for 72 hr. TNFα levels in culture supernatants were measured by ELISA. In brief, 96-well Immulon H2B plates were coated with anti-TNFα Ab (Genzyme, Cambridge, Mass.). Plates were blocked with PBS-1% BSA and overlaid with culture supernatants. Bound cytokine was detected by the addition of biotin labeled anti-TNFα Ab (Genzyme, Cambridge, Mass.) followed by phosphatase-conjugate avidin.

RT-PCR:

Total RNA was extracted from homogenized knees using TRIzol reagent (GibCO Life Technologies, Gaithersburg, Md.) as recommended by the manufacturer. 5 ug of total RNA was reverse transcribed into cDNA, which was assayed for TNFα (sense ATGAGCACAGAAAGCATGATC, antisense TACAGGCTTGTCACTCGAATT, 275 bp) and β-actin (sense GACATGGAGGAGTCTGGCACCACA, antisense ATCTCCTGCTCGAAGTCTAGAGCAA, 440 bp) by PCR as previously described (Takeshita et al., *Neuroreport* (2001) 12:3029-3032). Relative band intensity was determined by ethidium bromide staining of 1% agarose gels using NIH-Image software.

Statistical Analysis:

Statistically significant differences between two groups were determined using the Wilcoxon Rank Sum Test. When comparing more than two groups, a two-tailed non-parametric ANOVA with Dunn's post-test analysis was used. Differences in joint diameters were analyzed by repeated-measures ANOVA using the Proc Mixed procedure from the Statistical Analysis System (SAS). p values <0.05 were considered significant.

B. Induction of Arthritis by CpG ODN

Microbial infection of the gastrointestinal (GI) or genitourinary (GU) tracts is associated with the development of reactive arthritis in humans. Evidence suggests that bacterial DNA contributes to this process, since 1) bacterial DNA can be detected in arthritic joints (Braun et al., *J. Rheumatol.* (2000) 27:2185-2192), and 2) bacterial DNA induces joint inflammation when injected into the knees of normal mice (Deng et al., *Nat. Med.* (1999) 5:702-705). Deng et al. established that immunostimulatory CpG motifs were the cause of this inflammation by showing that CpG-containing oligodeoxynucleotides (ODN) induced disease in a manner similar to that induced by purified bacterial DNA (Deng et al., supra). This effect is consistent with the proinflammatory properties of CpG ODN, including their ability to stimulate immune cells to proliferate, differentiate, and secrete proinflammatory chemokines and cytokines (Deng et al., supra; Klinman et al., *Springer Semin. Immunopathol.* (2000) 22:173-83).

Figure 11A:
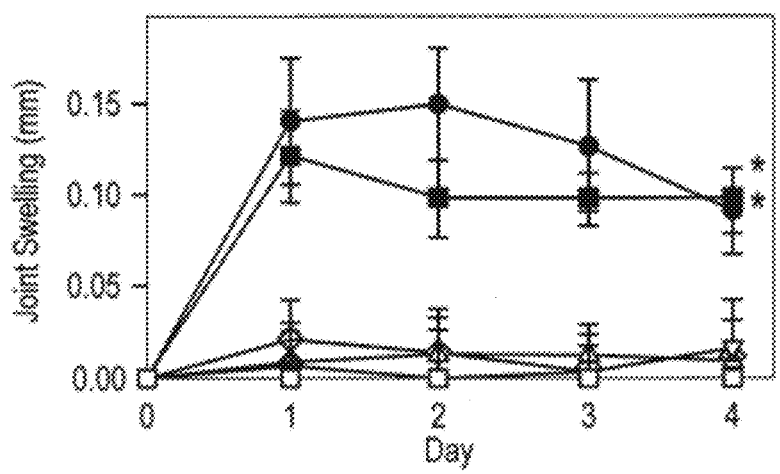
FIG. 11A is a graph of joint swelling in mice treated with CpG ODN (solid circle), CpG plus control ODN (solid square), CpG plus suppressive ODN (open diamond), control ODN (open triangle), suppressive ODN (inverted open triangle), or PBS (open square, N=8-11 mice/group).
Figure 11B:
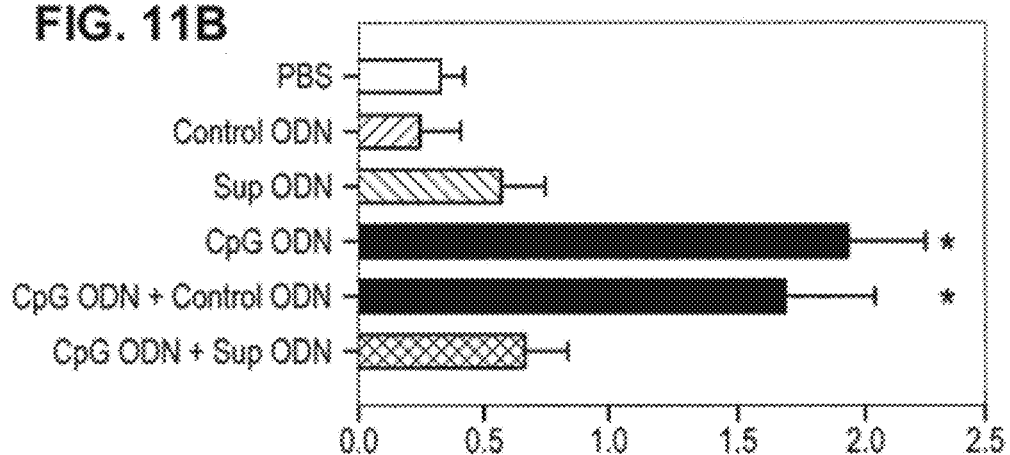
FIG. 11B is a graph showing histologic changes in the injected knees. Knees were evaluated 4 days after treatment by a blinded investigator. Scale: 0; no inflammation, 1; sparse, localized perivascular infiltrate, 2; moderate infiltrate, 3; moderate-dense infiltrate with synovial hyperplasia.
Figure 11C:
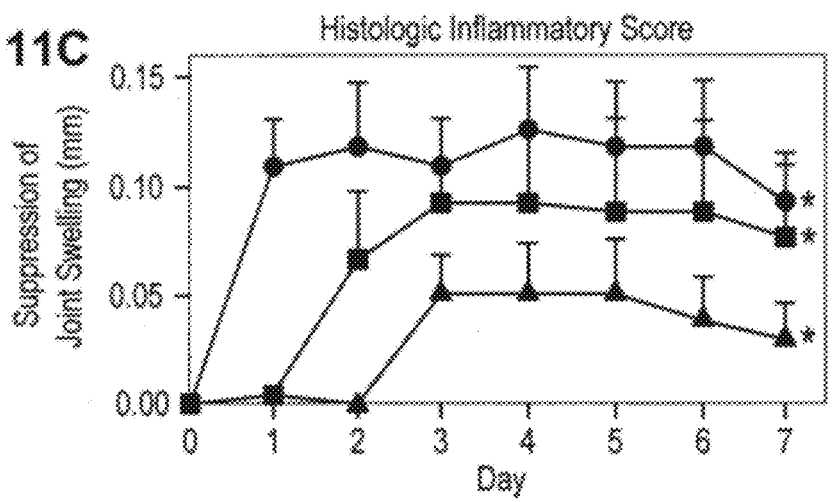
FIG. 11C is a graph showing that suppressive ODNs suppress joint swelling. At T=0, both knees were injected with 25 g of CpG ODN. The R knee was then injected with PBS and the L knee with 25 g of suppressive ODN either 0 (solid circles, N=3), 24 (solid squares, N=6) or 48 (solid triangles, N=6) h later. Results show the difference in swelling between the two knees. Statistical significance was assessed by repeated-measures ANOVA using the Proc Mixed procedure (A, C) and Wilcoxon Rank sum test (B). * p<0.05.

Consistent with the findings of Deng et al. (Deng et al., *Arthritis Rheum.* (2000) 43:356-364), BALB/c knees injected with CpG ODN developed inflammatory arthritis within 24 hr that peaked after 3-7 days (FIG. 11). CpG-induced arthritis was characterized by swelling (0.14+0.04 mm vs 0.02+0.02, p=0.054) and histological changes that included perivascular infiltration by mononuclear cells and hyperplasia of the synovial lining (FIG. 11). These inflammatory effects were CpG-specific and localized, since no disease was observed in contra-lateral knees injected with PBS or control ODN. Similar swelling and histologic changes were observed in knees injected with bacterial DNA.

C. Suppressive ODN Block the Development of CpG-induced Arthritis

To determine whether suppressive ODN prevent CpG mediated inflammatory arthritis, knees were co-injected with 25 g of suppressive plus 25 g of CpG ODN. The inclusion of suppressive ODN reduced swelling from 0.14+0.04 mm to 0.02+0.02 mm (p=0.004) and the inflammatory score from 1.94+0.32 to 0.67+0.12 (p=0.018, FIG. 11). When joint inflammation was assessed by magnetic resonance imaging, suppressive ODN reduced CpG ODN induced fluid accumulation from 95.4+8.2 MR-signal intensity units to 52.3+6.7 units (n=5, p<0.001). These effects were specific, since co-administering PBS or control ODN had no impact on CpG-induced arthritis (FIG. 11). In parallel studies, suppressive ODN prevented the arthritis induced by bacterial DNA but not LPS (data not shown).

D. Kinetics of the ODN Anti-inflammatory Effect

To examine the kinetics of this anti-inflammatory effect, suppressive ODN were administered 0, 24 and 48 h after CpG ODN injection. To control for the effect of multiple injections, the contralateral knee was injected with PBS, and the difference in swelling between the two joints evaluated daily. A significant reduction in swelling was observed when joints were treated with suppressive ODN up to two days after CpG administration (p=0.012, FIG. 11C). However, maximal control of arthritis required early intervention (p=0.011, D0 vs D2).

E. Suppressive ODNs Reduce Intra-articular TNF Production

Previous studies established that the magnitude of CpG-induced arthritis correlated with intra-articular TNFα levels (Deng et al., *Arthritis Res.* (2001) 3:48-53). Consistent with TNFα playing a critical role in the disease process, TNFα KO mice fail to develop CpG-induced arthritis (Deng et al., *Arthritis Rheum.* (2000) 43:356-364; Ronaghy et al., *J. Immunology* (2002) 168:51-56). To evaluate whether suppressive ODN had an effect on TNFα production, BALB/c spleen cells were stimulated in vitro with CpG+suppressive ODN. As seen in FIG. 12, suppressive ODN reduced TNFα production in a dose-dependent manner, whereas control ODN had no effect.

Figure 12A:
FIG. 12: is a digital image of a photomicrograph showing the effects of CpG and ODN injection on knee histology in mice. BALB/c knees were injected with PBS (FIG. 12A, B), CpG ODN (FIG. 12C, D), CpG plus control ODN (FIG. 12E, F) or CpG plus suppressive ODN (25 g of each ODN, FIG. 12G, H). Typical histology 4 days after injection of 25 μg of each ODN is shown. Note the cellular infiltrates, perivascular accumulation of mononuclear cells, and hyperplasia of the synovial lining in the knees of mice injected with CpG ODN. Panels A, C, E and G show 100× magnification; panels B, D, F, H show 400× magnification.
Figure 12B:
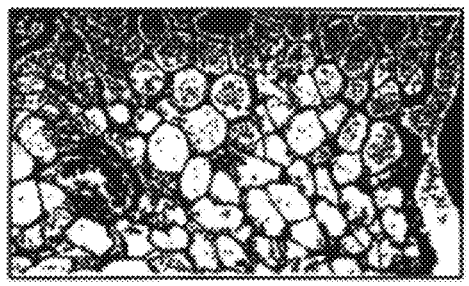
Figure 12C:
Figure 12D:
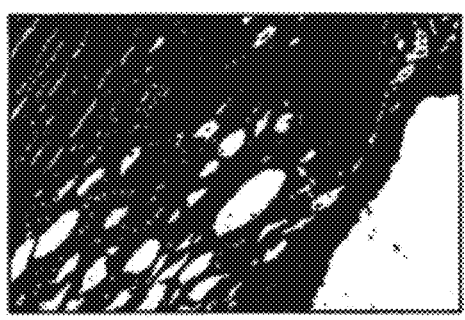
Figure 12E:
Figure 12F:
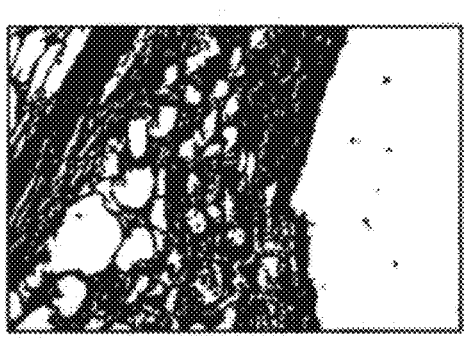
Figure 12G:
Figure 12H:
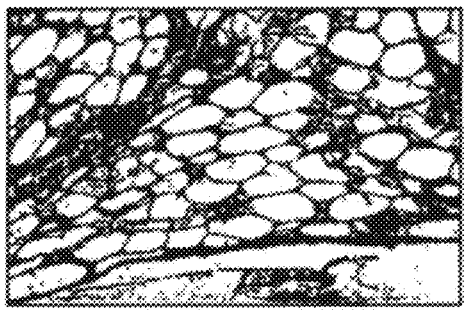
Figure 13A:
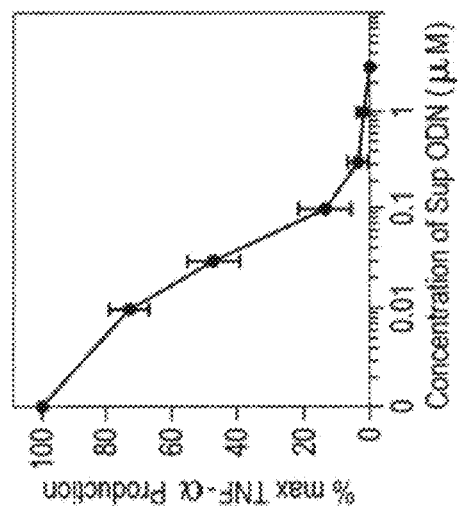
FIG. 13A is a graph of TNFα levels following treatment with ODN. BALB/c spleen cells were stimulated in vitro for 72 h with 1 μM of various ODN.
Figure 13B:
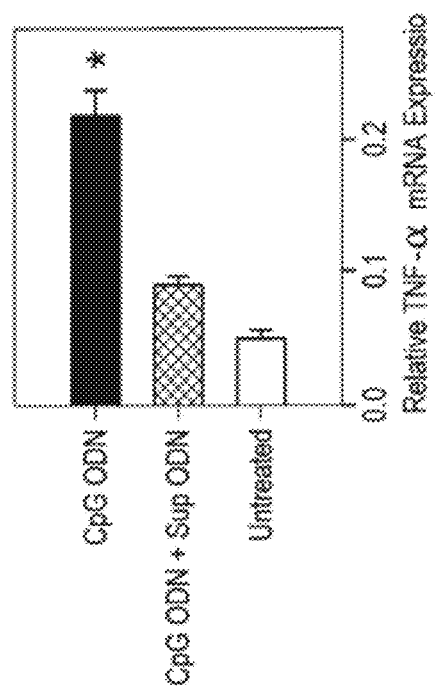
FIG. 13B is a graph of percent TNFα production versus suppressive ODN concentration. RAW 264.7 cells (106/well) were stimulated with 1 uM CpG plus increasing amounts of suppressive ODN. The concentration of TNF in culture supernatants after 24 h was measured by ELISA. Data represent the mean+SEM of 5 independently studied animals/group. Statistical significance was assessed by Wilcoxon Rank sum test.
Figure 13C:
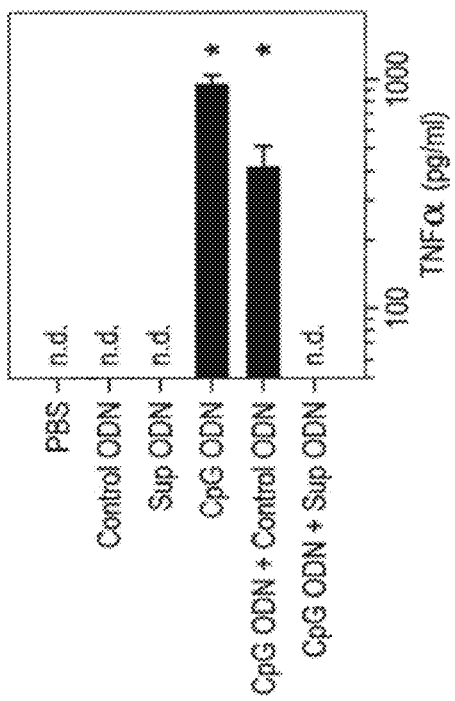
FIG. 13C is a digital image of an agarose gel. Joints injected with 25 g of ODN were processed into RNA 3 days later. Representative examples of local TNF and β-actin mRNA levels are shown.
Figure 13D:
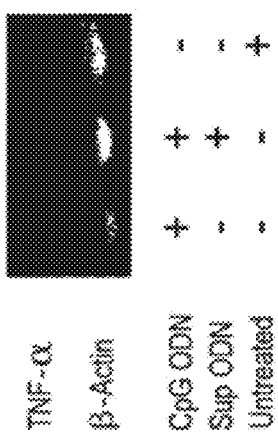
FIG. 13D is a graph of relative TNFα mRNA expression following treatment with CpG ODN or CpG ODN and suppressive ODN. Relative intensity of TNFα vs β-actin mRNA (N=3). * p<0.05.

To monitor the in vivo effect of suppressive ODN on TNF production, cytokine mRNA levels were measured in the joint. Consistent with earlier reports (Deng et al., *Arthritis Rheum.* (2000) 43:356-364; Ronaghy et al., *J. Immunology* (2002) 168:51-56; Kyburz et al., *Arthritis Rheum.* (2001) 44 (Suppl): S396), CpG ODN up-regulated local TNF mRNA levels (FIG. 12C, D). Co-administering suppressive ODN reduced TNFα mRNA by >50% (p<0.003, FIG. 12).

Example 6

Systemic Effect of Stimulatory and Suppressive Oligodeoxynucleotides on the Induction of Inflammatory Arthritis
A. General Methods
Animals:

Female BALB/c mice were obtained from the Jackson Laboratories (Bar Harbor, Me.). The mice were used at 8-20 weeks of age and were housed under specific pathogen free conditions. All experiments were approved by the CBER Animal Use and Care Committee.
Oligonucleotides:

ODN used in this study had a phosphorothioate backbone, and were synthesized in the CBER Core Facility. They contained <0.1 EU of endotoxin per mg of ODN, as assessed by a *Limulus amebocyte* lysate assay (QCL-1000, BioWhittaker). The sequence of the CpG ODN was GCTAGACGT-TAGCGT (SEQ. ID NO: 30), of the suppressive ODN: CCT-CAAGCTTGAGGGG (SEQ. ID NO: 1), and of the control ODN: GCTAGATGTTAGCGT (SEQ. ID NO: 31).
Experimental Protocols:

Arthritis was induced as previously described in Zeuner, R A, et al., *Arthritis Rheum.* (2002), in press. Briefly 1 or 25 μg of ODN in 6 μl of PBS was injected into the knee joint using a 30 gauge needle. Joint swelling was measured in the coronal plane using a micrometer caliper (General Tools Mfg CO, NY, N.Y.). Mice were euthanized on day 4 and the knees fixed, decalcified, sectioned, and stained with hematoxylin/eosin prior to histologic examination. Scoring was performed by a blinded investigator using a scale of 0-4. 0=absence of inflammation, 1=sparse, localized perivascular infiltrate, 2=moderate infiltrate, 3=moderate-dense infiltrate with synovial hyperplasia, 4=dense infiltrate with pronounced synovial hyperplasia.

In some experiments, donor mice were injected IP with 300 μg of ODN in PBS. A single cell suspension prepared from the spleens of these mice was prepared, and 20×106 transferred IV to naive littermate recipients. These spleen cells were enriched or depleted of various subpopulations using magnetic bead separation (Vario-Macs System, Miltenyi) as recommended by the manufacturer.
Statistical Analysis:

Differences between two groups determined using the Wilcoxon Rank Sum Test. Differences between multiple groups were evaluated using a two-tailed ANOVA on Ranks with Dunn's post test analysis. Differences in joint diameters were compared by repeated-measures ANOVA. P values <0.05 were considered significant. Data are presented as mean+SEM.F.
B. Effect of Systemic CpG ODN on Sensitivity of Joints to Inflammatory Stimuli Previous studies established that intra-articular injection of bacterial DNA or CpG ODN induces arthritis in mice, characterized by an inflammatory cell infiltrate, perivascular accumulation of mononuclear cells, and hyperplasia of the synovial lining Deng, G M, and Tarkowski A., *Arthritis Rheum.* (2000) 43:356-364. Since reactive arthritis in humans is associated with infection of the GI or GU tract rather than the joint, we explored whether CpG DNA in the systemic circulation might alter the sensitivity of joints to inflammatory stimuli.

Figure 14:
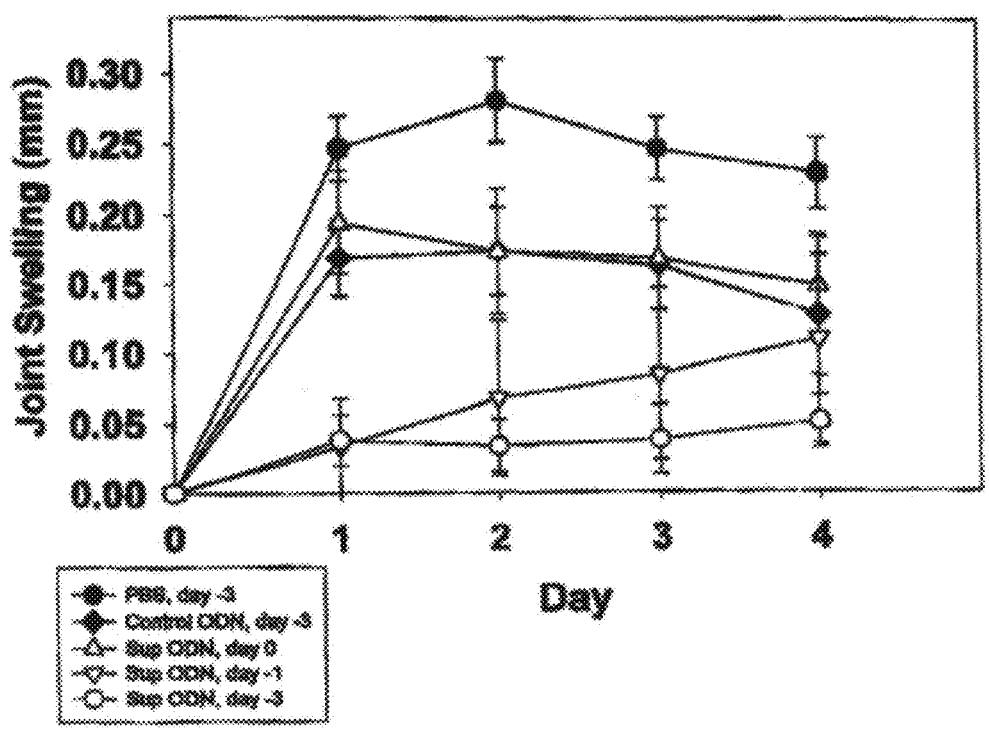
FIG. 14: is a graph showing that the local administration of suppressive ODNs reduces the pro-inflammatory effect of CpG ODN administration. Optimal suppression of CpG ODN-mediated joint inflammation is attained when the suppressive ODN are administered 3 days before the inflammatory challenge. Shown is the mean and SEM of 10-11 mice/group pre-treated locally (intra-articularly) with suppressive ODN 3 days prior to CpG ODN challenge (open circles), suppressive ODN administered 1 day prior to CpG ODN challenge (open, inverted triangles), suppressive ODN administered at the time of the CpG ODN challenge (open triangles). The joint swelling of mouse knees injected with control ODN (black diamonds) or PBS (black circles) 3 days before the CpG serve as controls.

To examine this possibility, normal BALB/c mice were injected IP with 300 ug of CpG DNA, and then challenged with a sub-arthritogenic dose of local CpG ODN. As seen in FIG. 14, normal mice and mice treated with PBS or control ODN did not develop arthritis (no inflammation, no swelling) when injected with 1 μg of CpG. In contrast, animals pretreated with systemic CpG DNA developed significant joint swelling, a mononuclear cell infiltrate, and synovial hyperplasia when challenged with the same dose of CpG ODN. These changes were triggered by exposure to local CpG DNA, as no inflammation developed when the joints of systemically treated animals were injected with PBS.

These findings indicate that CpG DNA in the systemic circulation (perhaps released by dying bacteria in the GI or GU tract) can increase the host's susceptibility to the development local arthritis.
C. Systemic Administration of Suppressive ODN Reduces Susceptibility to Arthritis It has been demonstrated that suppressive ODN (containing motifs that selectively inhibit the immunostimulatory activity of CpG ODN) significantly reduce the swelling, synovial hyperplasia and leukocyte infiltration induced by CpG DNA. These effects were observed when suppressive ODN were injected directly into arthritic joints. Based on the observation that systemic CpG DNA can increase the host's susceptibility to arthritis, we postulated that suppressive ODN in the systemic circulation might lower this susceptibility.

Figure 15:
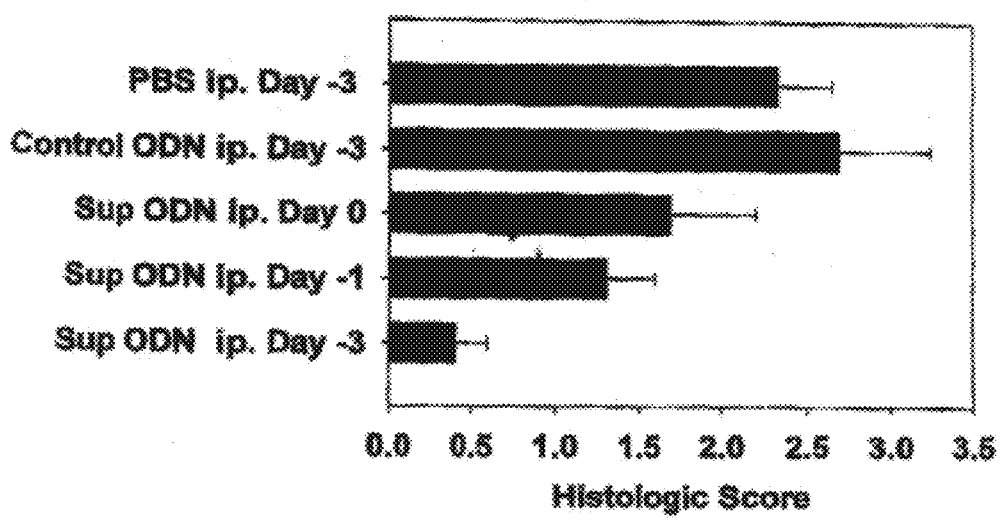
FIG. 15: is a graph showing that naive mice (and mice pre-treated with control ODN or PBS) developed severe arthritis following local CpG ODN challenge. In contrast, systemic administration of suppressive ODN three days prior to local CpG DNA challenge reduced joint swelling and inflammation by 80-85% (p<0.029). BALB/c mice were treated IP with 300 µg of suppressive ODN 0-3 days prior to the intra-articular injection of 25 µg CpG DNA. Consistent with previous studies, naive mice (and mice pre-treated with control ODN or PBS) developed severe arthritis following local CpG ODN challenge.
Figure 16A:
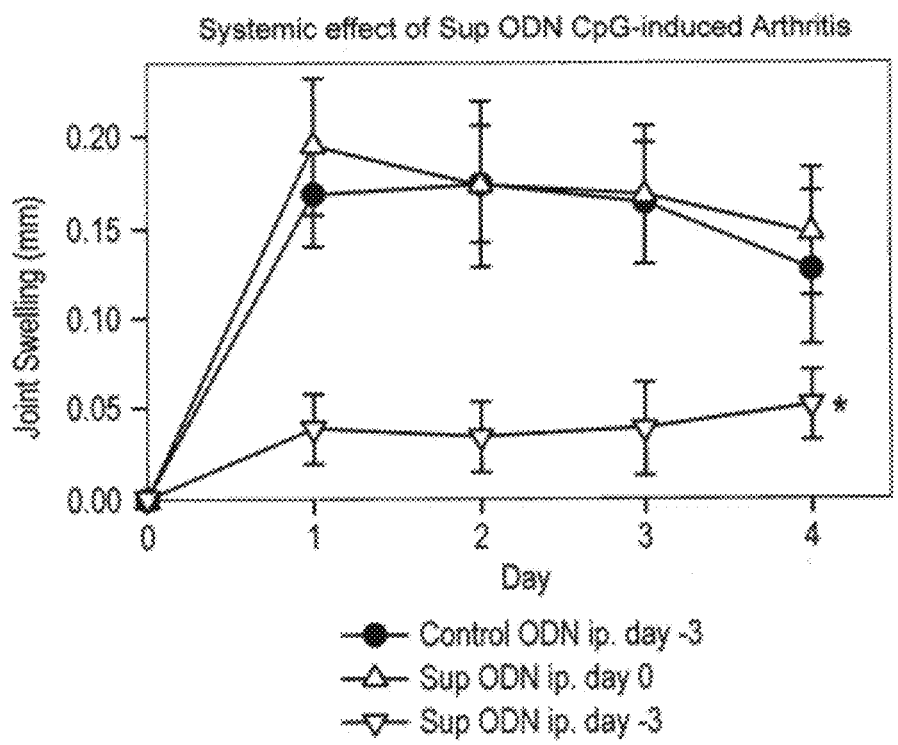
FIG. 16: is a pair of graphs showing that systemic administration of suppressive ODN three days prior to local CpG DNA challenge reduced joint swelling and inflammation by 80-85% (p<0.029).
Figure 16B:
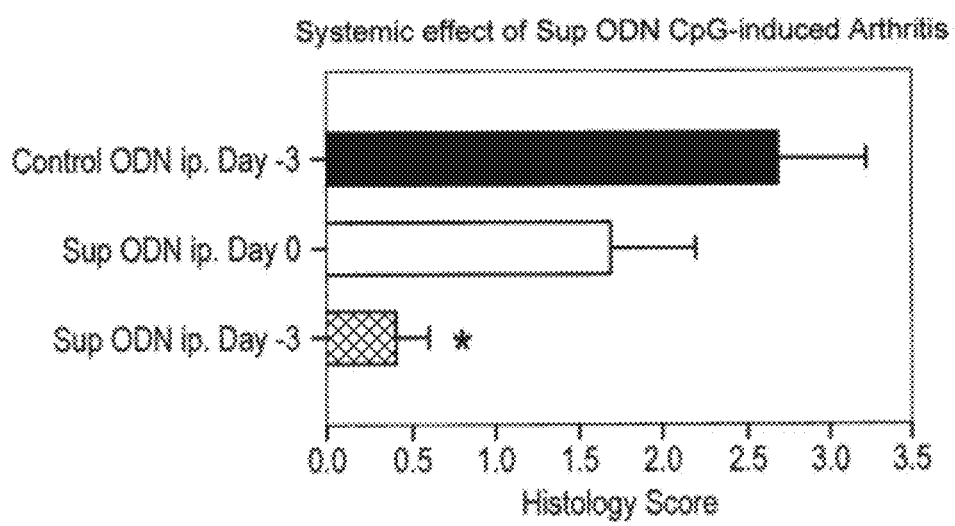
Figure 17A:
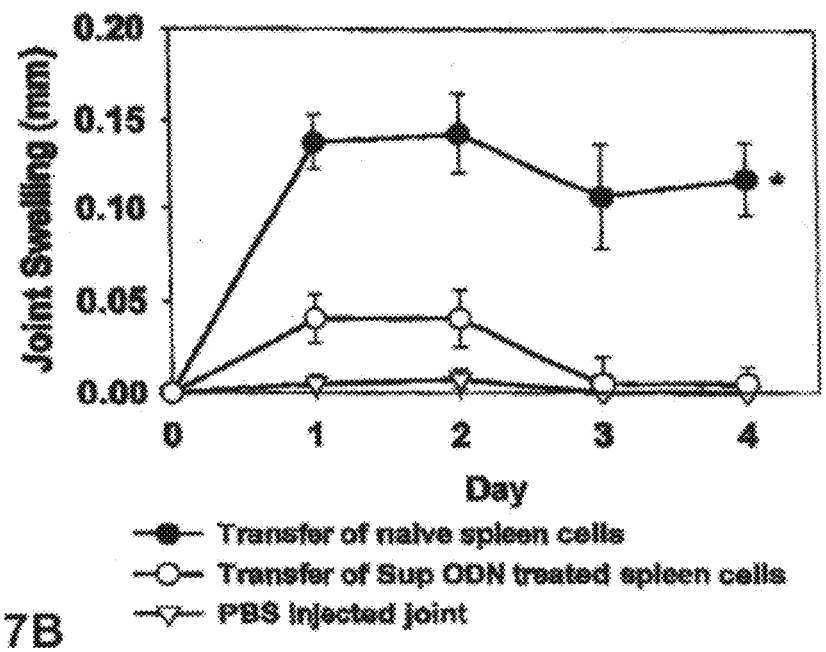
FIG. 17: is a pair of graphs showing that systemically administered suppressive ODN elicit a population of regulatory cells that inhibit CpG-induced arthritis. As expected, spleen cells from untreated donors had no effect on the development of CpG-induced arthritis. By comparison, the transfer of 20×10$^6$ spleen cells from suppressive ODN treated donors significantly reduced joint swelling and inflammation in the recipients.
Figure 17B:
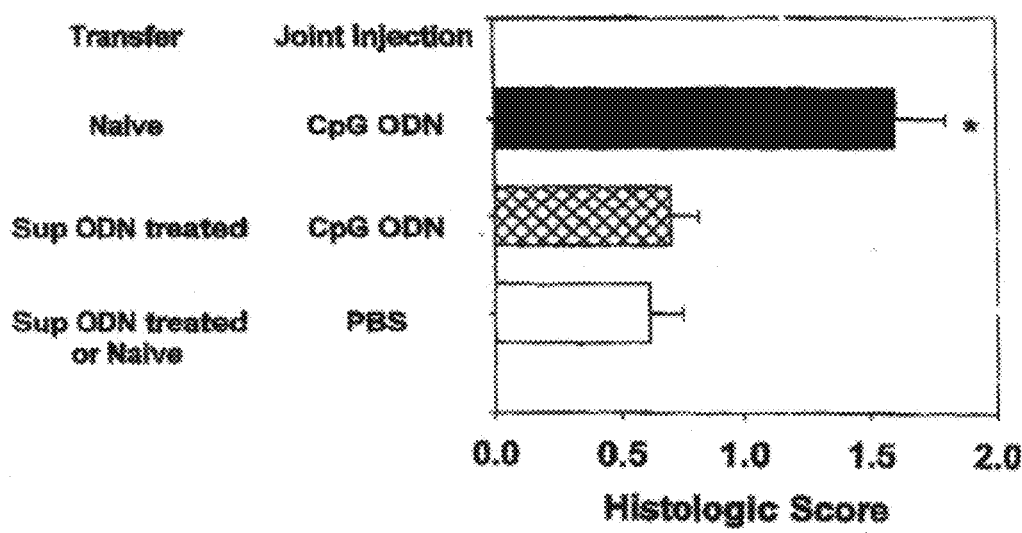

To test this hypothesis, BALB/c mice were treated IP with 300 ug of suppressive ODN 0-3 days prior to the intra-articular injection of 25 ug CpG DNA. Consistent with previous studies, naive mice (and mice pre-treated with control ODN or PBS) developed severe arthritis following local CpG ODN challenge (FIG. 15). In contrast, systemic administration of suppressive ODN three days prior to local CpG DNA challenge reduced joint swelling and inflammation by 80-85% (FIG. 16; p<0.029). Unlike the situation with locally administered suppressive ODN, which reduced inflammation when administered up to 2 days after the induction of arthritis, suppressive ODN were effective systemically only if delivered several days prior to the induction of arthritis. These findings suggest that instead of blocking CpG induced arthritis locally, suppressive ODN in the systemic circulation might activate a regulatory cascade that requires several days to mature.
D. Spleen Cells from Suppressive ODN Treated Mice Prevent CpG-induced Arthritis To investigate this possibility, spleen cells from mice treated systemically with suppressive ODN were transferred to naive controls, which were then injected with 25 ug of CpG DNA intra-articularly. As expected, spleen cells from untreated donors had no effect on the development of CpG-induced arthritis (FIG. 17). By comparison, the transfer of $20 \times 10^6$ spleen cells from suppressive ODN treated donors significantly reduced joint swelling and inflammation in the recipients. These findings indicate that systemically administered suppressive ODN elicit a population of regulatory cells that inhibit CpG-induced arthritis.

To define the time course over which these regulatory cells are generated, splenocytes were isolated from 1-3 days after treatment with suppressive ODN. Cells from animals treated with suppressive ODN for 3 days significantly inhibited CpG-induced arthritis, whereas splenocytes from animals exposed to suppressive ODN for shorter periods were progressively less effective.

Figure 18:
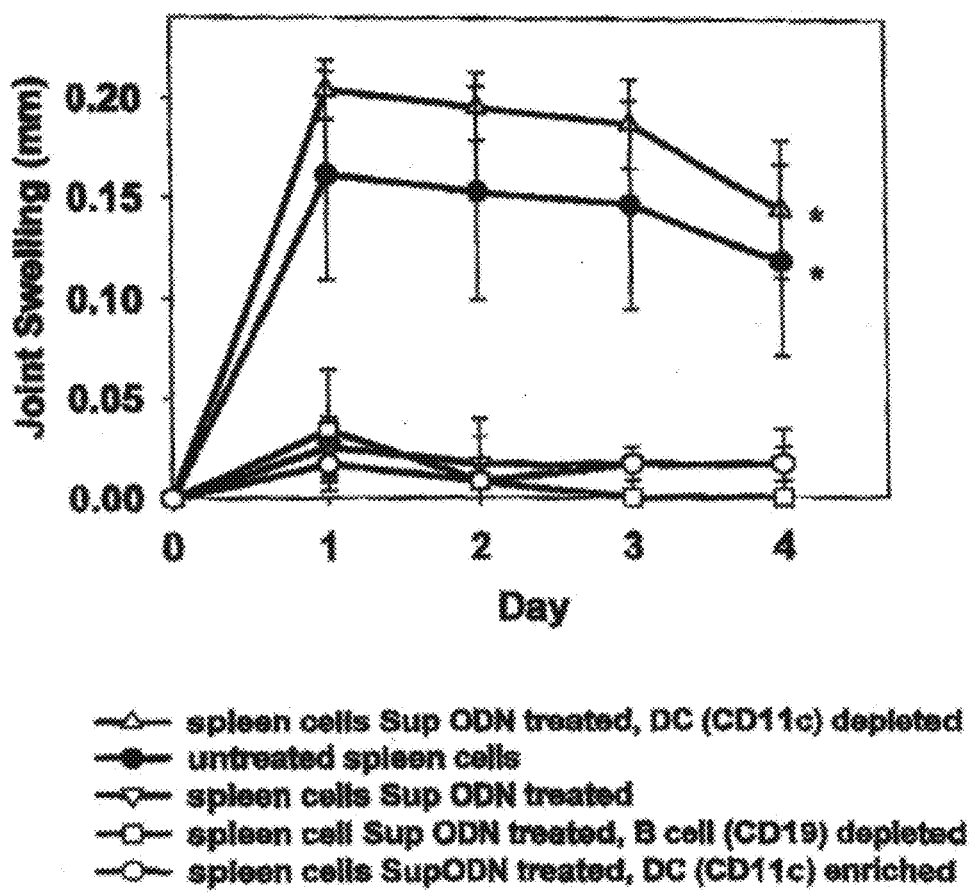
FIG. 18: is a graph showing that CD11c+ cells are responsible for the resistance to CpG-induced arthritis. Magnetic beads were used to deplete or enrich specific cell subpopulations from donor spleens. Depletion of CD 19+ B cells, T cells, or NK cells had no effect on CpG-induced arthritis. However, removal of CD11c+ dendritic cells resulted in a complete abrogation of the suppressive activity of the transferred spleen cell population. Similarly, the transfer of only 5×10$^5$ CD11c+ enriched cells from suppressive ODN treated mice to normal recipients conferred resistance to CpG-induced arthritis.

To characterize the cell type responsible for this resistance to CpG-induced arthritis, magnetic beads were used to deplete or enrich specific cell subpopulations from donor spleens. Depletion of CD19+ B cells, T cells, or NK cells had no effect on CpG-induced arthritis (FIG. 18). However, removal of CD11c+ dendritic cells resulted in a complete abrogation of the suppressive activity of the transferred spleen cell population. Similarly, the transfer of only 5×105 CD11c+ enriched cells from suppressive ODN treated mice to normal recipients conferred resistance to CpG-induced arthritis.

Example 7

Neutralizing ODN Inhibits HSV DNA-Induced Angiogenesis

A. General Methods

Phosphorothioate ODNs were synthesized at the Center for Biologics Evaluation and Research Core Facility, as described (Verthelyi et al., (2001) *J. Immunol.* 166, 2372-2377). The sequences of the stimulatory ODNs used in this study were: 1466, TCAACGTTGA (SEQ. ID NO: 26), and 1555, GCTAGACGTTAGCGT (SEQ ID No: 27); subsequent studies were conducted using an equimolar mixture of ODNs 1466 and 1555), the control ODN 1471 has the sequence TCAAGCTTGA (SEQ ID NO: 28), and the neutralizing ODN has the sequence GAGCAAGCTGGACCTTCCAT (SEQ ID NO: 20). There was no detectable endotoxin contamination in any of the ODNs, as monitored by *Limulus amebocyte* lysate assay (BioWhittaker). In some experiments, FITC was conjugated to the 5' end of these ODN to monitor their distribution in vivo.

Herring sperm DNA (Boehringer Mannheim) was prepared by passage through Detoxi-Gel Endotoxin Removal Gel 20344 (Pierce) to reduce endotoxin levels to <6 endotoxin units per mg. Recombinant human VEGF165 (rh-VEGF), recombinant mouse VEGF (rmVEGF), mouse VEGF-neutralizing antibody, and biotinylated rat anti-mouse VEGF were purchased from R & D Systems. Synthetic mesh and hydron polymer (type NCC) were purchased from Sefar America (Kansas City, Mo.) and Hydro Med Sciences (Cranbury, N.J.), respectively. Sucralfate was kindly provided by Bulch Meditec (Vaerlose, Denmark). Lipopolysaccharide was purchased from Sigma, and streptavidin-PE from PharMingen.

Isolation of HSV-1 DNA

Virus was harvested from infected Vero cells when the cytopathic effects were maximal, as described (Killington et al., (1996) in Virology Methods Manual, eds. Mahy, B. W. J. & Kangro, H. O. (Academic, New York), pp. 71-88; McCance, D. J. (1996) in Virology Methods Manual, eds. Mahy, B. W. J. & Kangro, H. O. (Academic, New York), pp. 191-197). Cells were suspended in sterile PBS and freeze-thawed three times to release viral particles. The virion-containing supernatant was then ultracentrifuged at 25,000×g for 90 min at 4° C., and the pellet suspended in sterile PBS. Viral particles were precipitated in a solution of 7% polyethylene glycol 8000 in 2.3% NaCl overnight at 4° C. and then centrifuged at 25,000×g. DNA was isolated from virions by treatment with 200 µg/ml proteinase K and 1% sarcosyl in STE buffer overnight at 56° C. The DNA was purified by multiple phenol/chloroform/isoamyl alcohol extractions, precipitated, sedimented at 12,000×g, dried, and resuspended in sterile STE buffer. RNA was removed by incubation with RNase (100 mg/ml; 5 Prime 3 Prime) for 1 h at 37° C., and the DNA reextracted as described above. The resultant material provided a single band by electrophoresis and contained undetectable protein (checked spectrophotometrically) or cellular DNA (measured by PCR for -actin DNA). All procedures were performed in a sterile environment, and all buffers and solutions were checked for the presence of lipopolysaccharide by using the Pyrogent plus test. No detectable protein, cellular RNA, or DNA, and less than 0.06 endotoxin units of endotoxin per mg of HSV DNA, were found.

Mice

Female BALB/c (Harlan-Sprague-Dawley) were used for all experiments. Animals were housed and cared for as described (Gangappa et al., (1998) *J. Immunol.* 161, 4289-4300).

Corneal Micropocket Assay

The murine corneal micropocket assay used in this work observed the general protocol of Kenyon et al. (Kenyon et al., (1996) *Invest. Ophthalmol. Vis. Sci.* 37, 1625-1632). Pellets 0.4×0.4×0.2 mm3 composed of sucralfate and hydron polymer were prepared (Kenyon et al., (1996) *Invest. Ophthalmol. Vis. Sci.* 37, 1625-1632). Known amounts of VEGF, DNA, stimulatory or neutralizing ODN, and/or combinations thereof were added to these pellets before insertion into corneal pockets. The micropockets were placed 0.6-0.8 mm from the limbus (in the pericenter of the cornea at the lateral canthus of the eye) under stereomicroscopy (four eyes per group). In some experiments, anti-mVEGF-neutralizing antibody (5 µg in 5 µl of PBS) was injected subconjunctivally into the eyes of recipient mice just before and 2 days after pellet implantation.

Angiogenesis was quantitated at multiple times after pellet implantation under stereomicroscopy. The length of the neovessels generated from the limbal vessel ring toward the center of the cornea and the width of the neovessels presented in clock hours (each clock hour is equal to 30° C. at the circumference) was measured (Zheng et al., (2001) *Am. J. Pathol.* 159, 1021-1029). The angiogenic area was calculated according to the formula for an ellipse. A=[(clock hours)×0.4×(vessel length in mm)×]/2.

Immunohistochemical Staining

Eyes were removed and snap frozen in OCT compound (Miles). Sections (6-µm) were cut, air dried, and fixed in cold acetone for 10 min. The sections were blocked with 3% BSA and stained with biotinylated anti-mVEGF164. Sections were then treated with horseradish peroxidase-conjugated streptavidin (1:1,000) and 3,3'-diaminobenzidine (Vector), and counterstained with hematoxylin as described (Zheng et al., (2001) *J. Virol.* 75, 9828-9835). Cellular infiltration was determined microscopically by counting the infiltrating cells in the corneal stroma. Each data point represents the mean total cellular infiltrate in four central corneal sections from two eyes.

VEGF Staining of J774A.1 Cells

J774A.1 cells were plated and incubated in two-well chamber slides (Lab-Tek, Nalge Nunc International) or in 24-well plates [for later reverse transcription (RT)-PCR] in DMEM with 10% FBS overnight at 37° C. in 5% CO2. The cells in chamber slides were cocultured with FITC-labeled CpG ODN (1555) or control ODN (1471) at a concentration of 2 µg/106 cells. The cells were washed twice with PBS and fixed in a 1:1 mixture of acetone/methyl alcohol at 20° C. for 15 min. The cells were stained with biotinylated rat-anti-mVEGF 6-18 h after ODN stimulation and subsequently reacted with streptavidin-PE. Images were taken by using a fluorescence microscope (Hamamatsu, Ichinocho, Japan). The cells in 24-well plates were treated with 2 µg of ODN per 106 cells per ml. RNA from these cells was extracted for RT-PCR to detect VEGF mRNA (see RNA Extraction and RT-PCR).

Fluorescence-Activated Cell Sorter Staining of VEGF-Expressing Cells

J774A.1 cells were treated with 0-8 μg/ml of ODN for 6-12 h. The cells were then fixed in paraformaldehyde, blocked with FCS, and stained for VEGF by using biotinylated rat-anti-mVEGF164 antibody followed by streptavidin-PE. Positive cells were identified by flow cytometry.

Statistical Analysis

Significant differences between groups were evaluated by using the Student's t test. P 0.05 was regarded as significant difference between two groups.

B. Neutralizing ODN Inhibits HSV DNA-Induced Angiogenesis

Figure 19:
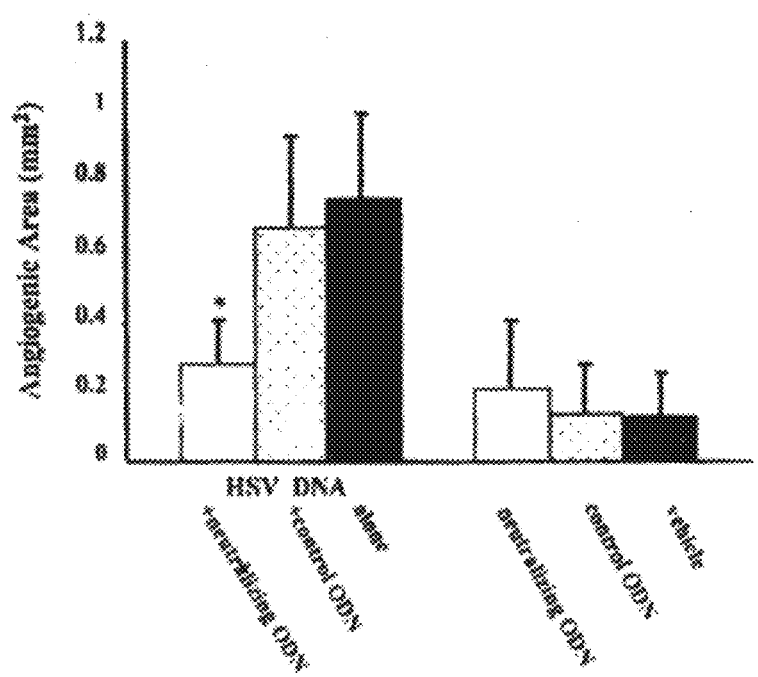
FIG. 19. is a graph showing that neutralizing ODNs inhibit HSV DNA-induced angiogenesis. Pellets containing 1 µg of HSV DNA alone or in combination with 1 µg of control or neutralizing ODN were implanted into corneal micropockets. The figure shows the average degree of angiogenesis 4 days after pellet implantation (four to five mice per group). *, P<0.01.

To investigate further whether CpG motifs in HSV DNA were responsible for the angiogenesis, HSV DNA was mixed with "neutralizing" or control ODN and the effect on angiogenesis recorded. The neutralizing ODN contained multiple G-tetrad-forming motifs that other studies have shown to neutralize the immunostimulatory effects of CpG DNA (Krieg et al., (1998) Proc. Natl. Acad. Sci. USA 95, 12631-12636; Lenert et al., (2001) Antisense Nucleic Acid Drug Dev. 11, 247-256; Pisetsky et al., (2000) Clin. Immunol. 96, 198-204). In these experiments, hydron pellets were prepared that contained HSV DNA along with neutralizing or control ODN. Levels of angiogenesis were recorded at 4 days after implantation. As is evident, pellets that incorporated control ODN plus HSV DNA induced the same level of angiogenesis as did HSV DNA pellets alone. In contrast, pellets containing neutralizing ODN plus HSV DNA induced significantly less (60% inhibition) angiogenesis ($P<0.01$, FIG. 19).

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the following claims:

We claim:

1. An oligodeoxynucleotide delivery complex comprising
   an oligodeoxynucleotide comprising the nucleic acid sequence set forth as SEQ ID NO: 3, wherein the oligodeoxynucleotide is modified to prevent degradation and wherein the oligodeoxynucleotide is at most 120 nucleotides in length, has a CD value of at least 2.9 and suppresses an immune response; and
   a targeting moiety.

2. The oligodeoxynucleotide delivery complex of claim 1, wherein the targeting moiety is selected from the group consisting of a cholesterol, a virosome, a liposome, a lipid, and a target cell specific binding agent.

3. The oligodeoxynucleotide delivery complex of claim 2, wherein the oligodeoxynucleotide and the targeting moiety are covalently linked.

4. The oligodeoxynucleotide delivery complex of claim 1, wherein the oligodeoxynucleotide consists of the nucleic acid sequence set forth as SEQ ID NO: 3.

5. The oligodeoxynucleotide delivery complex of claim 1, wherein the oligodeoxynucleotide has a CD value of greater than about 3.2.

6. The oligodeoxynucleotide delivery complex of claim 1, wherein the oligodeoxynucleotide is at most 30 nucleotides in length.

7. An immunosuppressive composition comprising an effective amount of
   an oligodeoxynucleotide comprising the nucleic acid sequence set forth as SEQ ID NO: 3, wherein the oligodeoxynucleotide is modified to prevent degradation and wherein the oligodeoxynucleotide is at most 120 nucleotides in length, has a CD value of at least 2.9 and suppresses an immune response;
   an additional agent; and
   a pharmacologically acceptable carrier,
   wherein the additional agent is an anti-inflammatory agent, an immunosuppressive agent, or an anti-arthritis agent, and wherein the composition suppresses an immune response in a subject.

8. The immunosuppressive composition of claim 7, wherein the oligodeoxynucleotide is 30 nucleotides in length.

9. The immunosuppressive composition of claim 7, wherein the immunosuppressive agent is a non-steroidal anti-inflammatory agent.

10. The immunosuppressive composition of claim 7, wherein the oligodeoxynucleotide consists of the nucleic acid sequence set forth as SEQ ID NO: 3.

11. The immunosuppressive composition of claim 7, wherein the oligodeoxynucleotide comprises at most 20 guanosine-rich sequences.

12. The immunosuppressive composition of claim 11, wherein the oligodeoxynucleotide comprises four guanosine-rich sequences.

13. A method of suppressing an immune response in a subject comprising
   administering a therapeutically effective amount of the immunosuppressive composition of claim 7 to a subject in which it is desirable to suppress an immune response, thereby suppressing the immune response in the subject.

14. The method of claim 13, wherein the oligodeoxynucleotide is administered topically, parenterally, orally, intravenously, intra-muscularly, sub-cutaneously, inhalationally, nasally, topically, or intra-articularly.

15. The method of claim 13, wherein the oligodeoxynucleotide is at most 30 nucleotides in length.

16. The method of claim 13, further comprising administering an additional anti-inflammatory or immunosuppressive agent to the subject.

17. The composition of claim 7, wherein the anti-inflammatory agent is as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, and rofecoxib, steroids, such as cortisone, dexamethasone, hydrocortisone, methylprednisolone, prednisolone, prednisone, and triamcinolone.

18. A method of suppressing an immune response in a subject comprising
   administering a therapeutically effective amount of the oligonucleotide delivery complex of claim 1 to a subject in which it is desirable to suppress an immune response, thereby suppressing the immune response in the subject.

* * * * *

SEQUENCE LISTING

<160> NUMBER OF SEQ ID NOS: 31

<210> SEQ ID NO 1
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 1
cctcaagctt gagggg                                              16

<210> SEQ ID NO 2
<211> LENGTH: 24
<212> TYPE: DNA
<213> ORGANISM: Artificial Sequence
<220> FEATURE:
<223> OTHER INFORMATION: Suppressive oligonucleotide

<400> SEQUENCE: 2
ttagggttag ggttagggtt aggg                                      24

<210> SEQ ID NO 3
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 3
ttagggttag ggttaggg                                             18

<210> SEQ ID NO 4
<211> LENGTH: 12
<212> TYPE: DNA
<213> ORGANISM: Artificial Sequence
<220> FEATURE:
<223> OTHER INFORMATION: Suppressive oligonucleotide -continued

```
<400> SEQUENCE: 4
ttagggttag gg                                                       12

<210> SEQ ID NO 5
<211> LENGTH: 24
<212> TYPE: DNA
<213> ORGANISM: Artificial Sequence
<220> FEATURE:
<223> OTHER INFORMATION: Suppressive oligonucleotide

<400> SEQUENCE: 5
tgggcggttg ggcggttggg cggt                                          24

<210> SEQ ID NO 6
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 6
tgggcggttg ggcggt                                                   16

<210> SEQ ID NO 7
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 7
tcaaccttca ttaggg                                                   16

<210> SEQ ID NO 8
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 8
ttagggttag ggtcaacctt ca                                            22

<210> SEQ ID NO 9
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 9
tcaaccttca ttagggttag gg                                            22

<210> SEQ ID NO 10
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 10
gggttagggt tatcaacctt ca                                            22

<210> SEQ ID NO 11
<211> LENGTH: 22
```

```
<212> TYPE: DNA
<213> ORGANISM: Artificial Sequence
<220> FEATURE:
<223> OTHER INFORMATION: Suppressive oligonucleotide

<400> SEQUENCE: 11
tcaaccttca gggttagggt ta                                        22

<210> SEQ ID NO 12
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 12
gggtgggtgg gtattaccat ta                                        22

<210> SEQ ID NO 13
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 13
attaccatta gggtgggtgg gt                                        22

<210> SEQ ID NO 14
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 14
tgggcggttc aagcttga                                             18

<210> SEQ ID NO 15
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 15
tcaagcttca tgggcggt                                             18

<210> SEQ ID NO 16
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 16
gggtgggtgg gtagacgtta cc                                        22

<210> SEQ ID NO 17
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 17 gggggggtcaa gcttca                                              16
```

<210> SEQ ID NO 18
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 18
tcaagcttca gggggg                                                     16

<210> SEQ ID NO 19
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 19
ggggggtcaa cgttca                                                     16

<210> SEQ ID NO 20
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 20
gagcaagctg gaccttccat                                                 20

<210> SEQ ID NO 21
<211> LENGTH: 21
<212> TYPE: DNA
<213> ORGANISM: Artificial Sequence
<220> FEATURE:
<223> OTHER INFORMATION: Suppressive oligonucleotide

<400> SEQUENCE: 21
gagcaagctg gtagacgtta g                                               21

<210> SEQ ID NO 22
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 22
gggcaagctg gacctggggg                                                 20

<210> SEQ ID NO 23
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 23
ggggaagctg gacctggggg                                                 20

<210> SEQ ID NO 24
<211> LENGTH: 20
<212> TYPE: DNA
<213> ORGANISM: Artificial Sequence
<220> FEATURE:
<223> OTHER INFORMATION: Suppressive oligonucleotide

```
<400> SEQUENCE: 24
gggcaagctg gaccttcggg                                               20

<210> SEQ ID NO 25
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 25
ggcaagctgg accttcgggg gg                                            22

<210> SEQ ID NO 26
<211> LENGTH: 10
<212> TYPE: DNA
<213> ORGANISM: Artificial Sequence
<220> FEATURE:
<223> OTHER INFORMATION: Immunostimulatory oligonucleotide

<400> SEQUENCE: 26
tcaacgttga                                                          10

<210> SEQ ID NO 27
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 27
gctagacgtt agcgt                                                    15

<210> SEQ ID NO 28
<211> LENGTH: 10
<212> TYPE: DNA
<213> ORGANISM: Artificial Sequence
<220> FEATURE:
<223> OTHER INFORMATION: Control oligonucleotide

<400> SEQUENCE: 28
tcaagcttga                                                          10

<210> SEQ ID NO 29
<211> LENGTH: 15
<212> TYPE: DNA
<213> ORGANISM: Artificial Sequence
<220> FEATURE:
<223> OTHER INFORMATION: Control oligonucleotide

<400> SEQUENCE: 29
gctagagctt aggct                                                    15

<210> SEQ ID NO 30
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 30
gctagacgtt agcgt                                                    15

<210> SEQ ID NO 31
<211> LENGTH: 15
```

-continued

```
<212> TYPE: DNA
<213> ORGANISM: Artificial Sequence
<220> FEATURE:
<223> OTHER INFORMATION: Control oligonucleotide

<400> SEQUENCE: 31
gctagatgtt agcgt                                                    15
```